US012661308B2

(12) United States Patent
Nair et al.

(10) Patent No.: US 12,661,308 B2
(45) Date of Patent: Jun. 23, 2026

(54) ANTIMICROBIAL AZO COMPOUNDS AND USES THEREOF

(71) Applicant: The Regents Of The University Of Colorado, A Body Corporate, Denver, CO (US)

(72) Inventors: Devatha P. Nair, Denver, CO (US); Dylan Mori, Denver, CO (US); Michael J. Schurr, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 1017 days.

(21) Appl. No.: 17/432,542

(22) PCT Filed: Feb. 21, 2020

(86) PCT No.: PCT/US2020/019364
§ 371 (c)(1),
(2) Date: Aug. 20, 2021

(87) PCT Pub. No.: WO2020/172632
PCT Pub. Date: Aug. 27, 2020

(65) Prior Publication Data

US 2022/0105011 A1 Apr. 7, 2022

Related U.S. Application Data

(60) Provisional application No. 62/808,699, filed on Feb. 21, 2019.

(51) Int. Cl.
*A61K 6/69* (2020.01)
*C07C 245/02* (2006.01)
*C08F 265/04* (2006.01)

(52) U.S. Cl.
CPC .............. *A61K 6/69* (2020.01); *C07C 245/02* (2013.01); *C08F 265/04* (2013.01)

(58) Field of Classification Search
CPC ............................. C07C 245/02; C08F 265/06
See application file for complete search history.

(56) References Cited

U.S. PATENT DOCUMENTS

| | | | | |
|---|---|---|---|---|
| 11,104,647 | B2 | 8/2021 | Sun et al. | |
| 11,540,909 | B2 | 1/2023 | Nair et al. | |
| 2005/0135454 | A1 | 6/2005 | Wu et al. | |
| 2008/0044472 | A1 | 2/2008 | Garcia et al. | |
| 2015/0094439 | A1 | 4/2015 | Tamura et al. | |
| 2015/0153479 | A1 * | 6/2015 | Iftime | G02B 1/04 |
| 2016/0313607 | A1 | 10/2016 | White et al. | |
| 2019/0146149 | A1 | 5/2019 | Aliberti et al. | |
| 2020/0262993 | A1 | 8/2020 | Nair et al. | |
| 2025/0127689 | A1 | 4/2025 | Nair et al. | |

FOREIGN PATENT DOCUMENTS

| | | | | |
|---|---|---|---|---|
| EP | 3162352 | A1 | 5/2017 | |
| WO | 2009003970 | A1 | 1/2009 | |
| WO | 2012035302 | A1 | 3/2012 | |
| WO | 2014162219 | A2 | 10/2014 | |
| WO | WO-2018099416 | A1 * | 6/2018 | C09B 69/10 |
| WO | 2023150010 | A3 | 10/2023 | |
| WO | 2024081755 | A2 | 4/2024 | |

OTHER PUBLICATIONS

M. Joseph et al, Reduction of Polyfunctional Aromatic Nitro Compounds Using Lithium Aluminum Hydride, Indian J. Chem., Sect. B: Org. Chem. Incl. Med. Chem. 43 (2004) 2, 432-436; Dep. Chem., Nirmala Coll., Muvattupuzha 686 661, Kerala, India; Eng. (Year: 2004).*

WO-2018099416-A1 (English translation, Google, downloaded Aug. 2025) (Year: 2025).*

Hu, et al., "Photomodulation of bacterial growth and biofilm formation using carbohydrate-based surfactants" Chem. Sci. 2016, vol. 7, pp. 6628-6634.

Li, et al., "The light-switching conductance of anisotropic azobenzene-based polymer close-packed on horizontally aligned carbon nanotubes" J. Mater. Chem. C, 2017, 5, (5068-5075).

Non-Final Office Action issued Jul. 18, 2022; U.S. Appl. No. 16/639,818; U.S. Filing Date Feb. 18, 2020 (6 pages).

Jeanneau et al., "Potential Therapeutic Strategy of Targeting Pulp Fibroblasts in Dentin-Pulp Regeneration", J. Endod, 2017 , 1-8, especially: abstract.

Li et al., "Photoresponsive behavior and switchable nonlinear optical properties of Langmuir-Blodgett film based on azobenzene derivatives," Optics Express, 2017, vol. 25, No. 10, pp. 1-11.

Mori et al., "Acrylated hydroxyazobenzene copolymer in composite-resin matrix inhibits S. mutans biofilms in vitro" Pediatr Dent., 2021, 43(6): 484-491, entire document.

Okiji et al., "Reparative Dentinogenesis Inducted by Mineral Trioxide Aggregate [MTA]: A Review from the Biological and Physiochemical Points of View," International Journal of Dentistry, 2009, article ID 464280, 12 pages.

Pang et al., "Photodeformable Azobenzene-Containing Liquid Crystal Polyers and Soft Actuators" Adv. Mater, 2019, 31, 1904224, 26 pages especially: abstract p. 3 Figure 1a, p. 12, col. 2, para 1.

(Continued)

*Primary Examiner* — Mark V Stevens
(74) *Attorney, Agent, or Firm* — CANTOR COLBURN LLP

(57) ABSTRACT

Antimicrobial azo compounds include azobenzene monomers having a phenyl ring comprising a hydroxyl substituent group. The azobenzene monomers can be reacted with a polymeric material to form an antimicrobial coating that prevents growth of persistent biofilms. In some implementations, the azobenzene monomers can be used to coat the surface of a dental resin-based composite to prevent the formation secondary caries. In some implementations, the azobenzene coating can be used to disperse microbial biofilms through a photofluidization process (rapid photoisomerization) in addition to biochemically preventing formation of the microbial biofilm.

16 Claims, 20 Drawing Sheets

(56) References Cited

OTHER PUBLICATIONS

Vidovic et al., "αSMA-Expressing Perivascular Cells Represent Dental Pulp Progenitors In Vivo," Journal of Dental Research, 2017, vol. 96, issue 3, pp. 323-330.
Ding et al., New azo-chromophore-containing multiblock poly(butadiene)s synthesized by the combination of wing-opening metathesis polymerization and click chemistry, Polymer, Feb. 6, 2010, pp. 1285-1292, vol. 51.
Do, T., et al., "Population structure of *Streptococcus oralis*," Microbiology (2009), 155, pp. 2593-2602.
Jeong, SP, et al., "High Energy Density in Azobenzene-based Materials for Photo-Thermal Batteries via Controlled Polymer Architecture and Polymer-Solvent Interactions," Scientific Reports, (2017) 7:17773 | DOI: 10.1038/s41598-017-17906-w, pp. 1-13.
Li et al., "Design and Applications of Photoresponsive Hydrogels," Advanced Materials, Mar. 8, 2019, vol. 31, 17 pages.
Trivedi et al., "Synthesis, characterization and evaluation of azobenzene nanogels for their antibacterial properties in adhesive dentistry," European Journal of Oral Sciences, Author manuscript, Dec. 19, 2021, vol. 130, 21 pages.
U.S. Appl. No. 19/117,295, filed Mar. 31, 2025; Inventors Devatha P. Nair, Dixa Gautam, Rinku Trevedi, Jeffrey Stansbury; Applicant Regents of the University of Colorado; Title Photoresponsive Azobenzene Functional Nanogels and Their Use in Dental Adhesives.
Bian, et al., "Light-Triggered Specific Cancer Cell Release from Cyclodextrin/Azobenzene and Aptamer-Modified Substrate" ACS Applied Materials & Interfaces, 2016, vol. 8, 27360-27367.
Hu, et al., "Photomodulation of bacterial growth and biofilm formation using carboydrate-based surfactants" Chemical Science, 2016, vol. 7, (pp. 6628-6634).
International Search Report mailed Jan. 4, 2019; Intemational Application No. PCT/US2018/047212; Intemational Filing Date Aug. 21, 2018 (4 pages).
International Search Report mailed Apr. 24, 2020; International Application No. PCT/US2020/19364; International Filing Date Feb. 21, 2020 (2 pgs).
Kehe, et al., "Optically Responsive, Smart Anti-Bacterial Coatings via the Photofluidization of Azobenzenes" ACS Appl Mater Interfaces, vol. 11, No. 2, Jan. 16, 2019, published online Jan. 4, 2019.
Li et al., "The light-switching conductance of an anisotropic azobenzene-based polymer close-packed on horizontally aligned carbon nanotubes" J. Mater. Chem. C, 2017, vol. 5 (5068-5075).
Pubchem (2-Phenyldiazenylphenyl) prop-2-enoate. Dec. 5, 2007, pp. 1-10 [online]; https://pubchem.ncbi.ilm.nih.gov/compound/19862056#/section=WIPO-IPC>; p. 2.
Written Opinion mailed Jan. 4, 2019; International Application No. PCT/US2018/047212; International Filing Date Aug. 21, 2018 (7 pages).
Written Opinion mailed Apr. 24, 2020; International Application No. PCT/US2020/19364; International Filing Date Feb. 21, 2020 (13 pgs).

* cited by examiner a) $R_1$ = OH, $R_2$ = H, $R_3$ = H, $R_4$ =

, $R_5$ = H b) $R_1$ = H, $R_2$ = OH, $R_3$ = OH, $R_4$ = H, $R_5$ =

HBA (A) (B)

| Time (h) | d (1) (mm) | d (2) (mm) | d (3) (mm) | d (LF) (mm) | d (U) (mm) | d (W) (mm) |
|---|---|---|---|---|---|---|
| 2 | 0 | 0 | 0 | 41 | 0 | 0 |
| 4 | 0 | 0 | 0 | 45 | 0 | 0 |
| 6 | 0 | 0 | 0 | 45 | 0 | 0 |
| 8 | 0 | 0 | 0 | 44 | 0 | 0 |
| 12 | 0 | 0 | 0 | 49 | 0 | 0 |

(A)

(B)

(C)

(A)

(B)

(C)

(D)

(A)

(B)

(C)

ANTIMICROBIAL AZO COMPOUNDS AND USES THEREOF

CROSS-REFERENCE TO RELATED APPLICATIONS

This application is a National Stage application of PCT/US2020/019364, filed Feb. 21, 2020, which claims the benefit of U.S. Provisional Application No. 62/808,699, filed Feb. 21, 2019, both of which are incorporated by reference herein in their entirety.

STATEMENT REGARDING FEDERALLY SPONSORED RESEARCH OR DEVELOPMENT

This invention was made with government support under Grant No. K25DE027418 awarded by the National Institutes of Health. The U.S. government has certain rights in the invention

BACKGROUND OF INVENTION

Tooth decay, or dental caries, is one of the most common preventable diseases in the world today, and it can lead to severe pain, mouth infection, and malnutrition. Dental caries affect billions of people worldwide and are the fourth-most expensive chronic disease to treat. As a result, dental caries often require lifelong treatment and care. The use of a restorative material, such as a composite polymeric filling, in treating dental caries is often responsible for the formation of secondary caries (caries that occur on previously established dental restorative materials), as polymeric stress and shrinkage of the filling can introduce new cariogenic bacteria into the filling.

Secondary caries are responsible for 60-75% of all operative work involving restorative materials, and they often require lifelong management. The interfaces of these restorative materials, usually consisting of a polymer resin filling, provide an ideal location for oral biofilm growth due to polymeric stress and crack formation. These oral biofilms often lead to tooth demineralization and, ultimately, secondary caries, and thus there is a need to develop restorative materials that discourage biofilm growth.

A specific challenge to the disruption of oral biofilms is the sucrose-dependent colonization and growth of *Streptococcus mutans* (*S. mutans*) oral biofilms. This biofilm consumes carbohydrates to form an extracellular polysaccharide matrix that increases adhesion to the enamel. In the case of *S. mutans*, once formed, the biofilm consumes sucrose to form lactic acid, which demineralizes the tooth. These biofilms are too robust and adhesive to be removed using current recommended treatment methods.

Current methods for oral biofilm removal include conventional dental hygiene practices, such as brushing and using mouthwash, and preventative measures, such as regularly ingesting fluoride and reducing sugar intake, but these methods rely primarily on public compliance and very rarely are effective at removing all residual bacteria. Antibiotics, such as penicillin, have been observed to target Gram-positive bacteria like *S. mutans*, but overuse of such antibiotics is not advisable because it could lead to the evolution of antibiotic-resistant strains over time.

Other dental coatings have incorporated antibacterial nanoparticles and cationic macromolecules in order to discourage *S. mutans* growth, but these materials have limited biocompatibility. The antibacterial nanoparticles, often consisting of silver, have reported cytotoxicity, while the cationic macromolecules, typically composed of quaternary ammonium groups, have reported hemolytic activity.

Some conventional resin materials increase the cariogenicity of bacteria leading to the occurrence of secondary caries at the composite-dentin interface. The matrix material can cause an increase of glycosyltransferase in *S. mutans* bacteria, which results in increased production of sticky glucans that allow *S. mutans* to adhere to the tooth. This results in cariogenic biofilms forming at the interface of composite and tooth.

SUMMARY OF INVENTION

Azobenzene compounds having hydroxyl substituent groups can be used to increase the antimicrobial properties of a variety of materials. For example, an azobenzene monomer can be reacted with a polymeric material to produce azobenzene pendant groups including at least one hydroxyl substituent group. The azobenzene pendant groups are preferably positioned on the surface of the polymeric material.

The azobenzene material can be used to prevent or substantially inhibit microbial growth on various surfaces, especially growth of *S. mutans*. It can also be used to remove live or dead microbes that may build up on the surface. This can be done by exposing the azobenzene material to various wavelengths in the visible light spectrum causing the azo material to undergo rapid trans-cis-trans isomerization thereby generating a photofluidization effect that loosens and removes microbial growth.

In some implementations, the azobenzene material is used to coat the surface of a dental resin-based composite material. The azobenzene material prevents and/or removes microbial growth that may cause secondary caries.

The term "(meth)acrylate" includes acrylates and/or methacrylates. The term "azobenzene" is used broadly as an adjective—e.g., azobenzene group, azobenzene monomer, azobenzene material, and the like—to refer to any such material comprising two phenyl rings linked by an N═N double bond where the phenyl rings can include any suitable substituent atoms, groups, chains, or the like.

The compositions, systems, and methods of this disclosure each have several innovative aspects, no single one of which is solely responsible for the described desirable attributes. The summary is provided to introduce a selection of concepts in a simplified form that are further described below in the detailed description. The summary and the background are not intended to identify key concepts or essential aspects of the disclosed subject matter, nor should they be used to constrict or limit the scope of the claims. For example, the scope of the claims should not be limited based on whether the recited subject matter includes any or all aspects noted in the summary and/or addresses any of the issues noted in the background.

Am embodiment of the present invention is directed to a method comprising reacting an azobenzene monomer with a polymeric material to form a polymeric composition having an azobenzene pendant group, wherein the azobenzene pendant group includes a phenyl ring having a hydroxyl substituent group.

Said method further comprising polymerizing at least two (meth)acrylate monomers to form the polymeric material.

Said method, wherein the at least two (meth)acrylate monomers include at least one di(meth)acrylate monomer.

Said method, wherein the polymeric material includes a dental resin-based composite.

Said method, wherein the polymeric material includes a polymeric substrate; and the reaction of the azobenzene monomer with the polymeric material includes reacting the azobenzene monomer with a surface of the polymeric substrate.

Said method, wherein the azobenzene monomer comprises an azobenzene (meth)acrylate monomer.

Said method, wherein the polymeric material comprises poly(meth)acrylate.

Said method, wherein the azobenzene pendant group includes at least two hydroxyl substituent groups attached to one or more phenyl rings.

Said method, wherein the azobenzene monomer has the following structure:

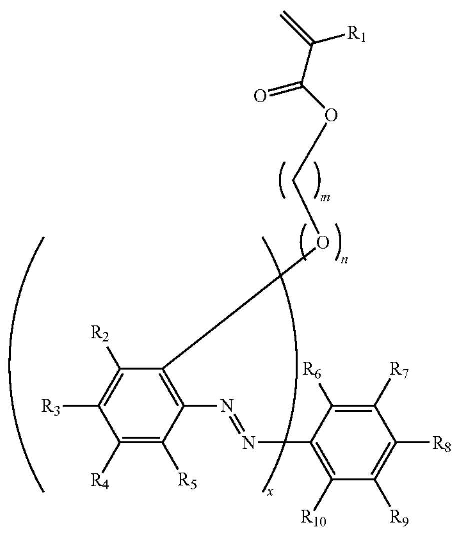

wherein:

n is 0 or 1;

m is an integer from 0 to 20;

x is an integer from 1 to 10;

R1 is H or methyl; and

R2, R3, R4, R5, R6, R7, R8, R9, and R10 are independently selected from H, methyl, and hydroxyl, and wherein at least one of R2, R3, R4, R5, R6, R7, R8, R9, or R10 is hydroxyl.

Said method, wherein n is 0 and m is 0.

Said method, wherein x is 1.

Said method, wherein at least one of R7, R8, or R9 is hydroxyl.

Said method, wherein n is 0, m is 0, x is 1, and at least one of R7, R8, or R9 is hydroxyl.

Said method, further comprising reacting another azobenzene monomer with the polymeric material.

Said method, wherein the azobenzene monomer has the following structure:

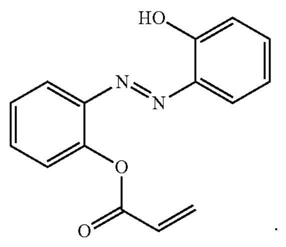 [SMILES: C=CC(=O)Oc1ccccc1/N=N/c1ccccc1O]

An embodiment of the present invention is directed to a method comprising coating a dental resin-based composite with an azobenzene material, wherein the azobenzene material is covalently bonded to the dental resin-based composite and includes a phenyl ring having a hydroxyl substituent group.

Said method further comprising polymerizing at least two (meth)acrylate monomers to form the dental resin-based composite.

Said method, wherein the at least two (meth)acrylate monomers include at least one di(meth)acrylate monomer.

Said method, wherein coating the dental resin-based composite with an azobenzene material comprises reacting an azobenzene monomer with the dental resin-based composite.

Said method, wherein the azobenzene material includes at least two hydroxyl substituent groups attached to one or more phenyl rings.

Said method, wherein the azobenzene material includes an azobenzene pendant group having the following structure:

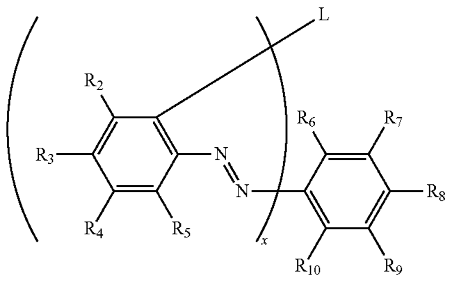

wherein:

x is an integer from 1 to 10;

L is a linking group that links the structure to the dental resin-based composite; and R2, R3, R4, R5, R6, R7, R8, R9, and R10 are independently selected from H, methyl, and hydroxyl, and wherein at least one of R2, R3, R4, R5, R6, R7, R8, R9, or R10 is hydroxyl.

Said method, wherein L is a (meth)acrylate linking group.

Said method, wherein x is 1.

Said method, wherein at least one of R7, R8, or R9 is hydroxyl.

Said method, wherein x is 1, L is a (meth)acrylate linking group, and at least one of R7, R8, or R9 is hydroxyl.

Said method, wherein x is 1, L is a (meth)acrylate linking group; and at least R6 is hydroxyl.

Said method, wherein the azobenzene material includes an azobenzene pendant group having the following structure:

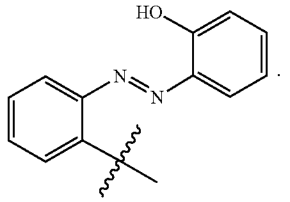 [SMILES: *c1ccccc1/N=N/c1ccccc1O]

Said method, wherein the azobenzene material includes at least two azobenzene monomers.

An embodiment of the present invention is directed to a polymeric composition comprising: a polymer chain; and an azobenzene pendant group attached to the polymer chain, wherein the azobenzene pendant group includes a phenyl ring having a hydroxyl substituent group.

Said polymeric composition, wherein the polymer chain includes at least two (meth)acrylate monomers.

Said polymeric composition, wherein the at least two (meth)acrylate monomers include at least one di(meth) acrylate monomer.

Said polymeric composition, wherein the polymer composition is part of a dental resin-based composite.

Said polymeric composition, wherein the polymer chain is a constituent of a polymeric substrate, and wherein the azobenzene pendant group is attached to a surface of the polymeric substrate.

Said polymeric composition, wherein the azobenzene pendant group is an azobenzene (meth)acrylate pendant group.

Said polymeric composition, wherein the polymer chain includes poly(meth)acrylate.

Said polymeric composition, wherein the azobenzene pendant group includes at least two hydroxyl substituent groups attached to one or more phenyl rings.

Said polymeric composition, wherein the azobenzene pendant group has the above-described structures.

An embodiment of the present invention is directed to a coated dental resin-based composite comprising: a polymeric substrate; and an azobenzene pendant group attached to the polymeric substrate, wherein the azobenzene pendant group is as set forth above.

An embodiment of the present invention is directed to a method comprising reacting an azobenzene monomer with a polymeric material to form a polymeric composition having an azobenzene pendant group, wherein the azobenzene monomer has the following structure:

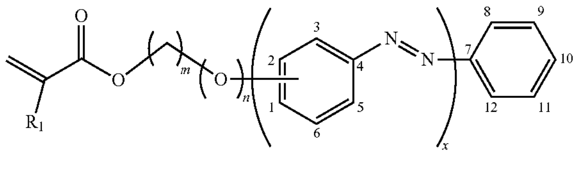

wherein:

n is 0 or 1;

m is an integer from 0 to 20;

x is an integer from 1 to 10;

R1 is H or methyl; and the hydrogen atoms bound to each of the ring carbon atoms at positions 1, 2, 3, 5, 6, 8, 9, 10, 11, and 12, to which the acrylate functional group that comprises R1 is not bound, are independently substituted with methyl or hydroxyl; and wherein at least one of said ring carbon atoms is substituted with hydroxyl.

Embodiments of the present invention are directed to methods, polymeric compositions, and coated dental resin-based composite comprising an azobenzene pendant group, wherein the azobenzene pendant has the following structure:

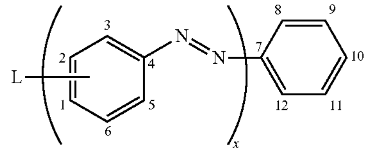

wherein:

x is an integer from 1 to 10;

L is a linking group that links the structure to the dental resin-based composite; and the hydrogen atoms bound to each of the ring carbon atoms at positions 1, 2, 3, 5, 6, 8, 9, 10, 11, and 12, to which the acrylate functional group that comprises R1 is not bound, are independently substituted with methyl or hydroxyl; and wherein at least one of said ring carbon atoms is substituted with hydroxyl.

BRIEF DESCRIPTION OF THE DRAWINGS

The preferred and other implementations are disclosed in association with the accompanying drawings.

FIG. 4(A) and (B) show a biofilm grown on an AAZO-coated substrate before and after the wash/light treatment, respectively. FIG. 4 (C) and (D) show a biofilm grown on an OH-AAZO-coated substrate before and after the wash/light treatment, respectively.

FIG. 12 is a table of a leaching study (Kirby-Bauer assay) of kill zone diameters of sampled media over time, wherein d=diameter of zone of inhibition for three (3) different samplings of media wells containing OH-AAZO substrates and one uncoated (U) well, LF=LevoFloxacin (positive control, 2.5 mg/mL solution), sterile MilliQ water (W) (negative control). No leaching of OH-AAZO monomer was detected.

In the bulk materials, both concentrations of OH-AAZO tested (1.5 wt. % and 2.0 wt. % OH-AAZO) maintained sterility in both the substrate and the surrounding media. Digital microscope images of *S. mutans* bacteria growing on both uncoated and coated bisGMA:TEGDMA substrates (the (B) and (C) images, respectively).

Figure 21:
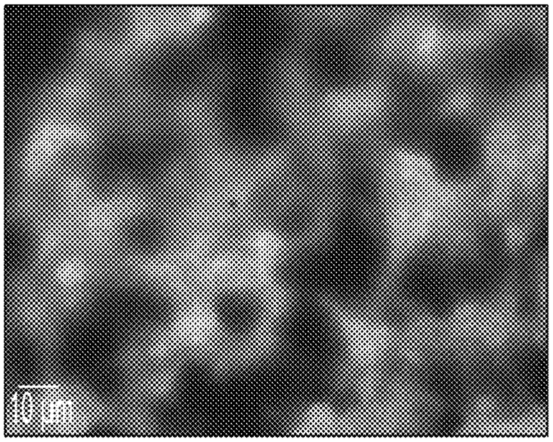
Figure 21:
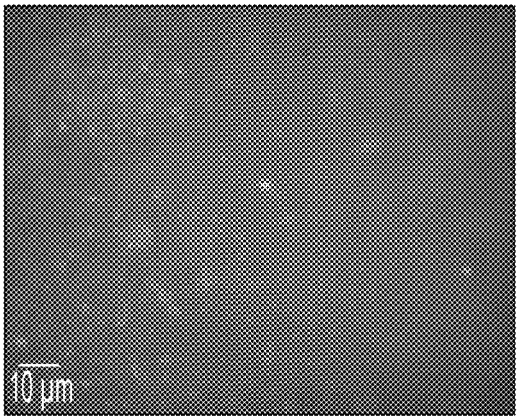
Figure 21:
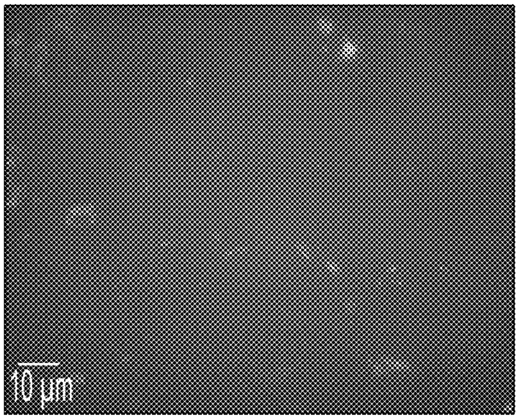

FIG. 21 are digital microscropy images of live-dead staining of biofilms on (A) uncoated substrate, (B) 1.5% OH-AAZO bulk substrate, and (C) 2% OH-AAZO bulk substrate, which shows that *S mutans* did not grow on the 1.5 and 2 wt % OH-AAZO bulk substrates.

Figure 22:
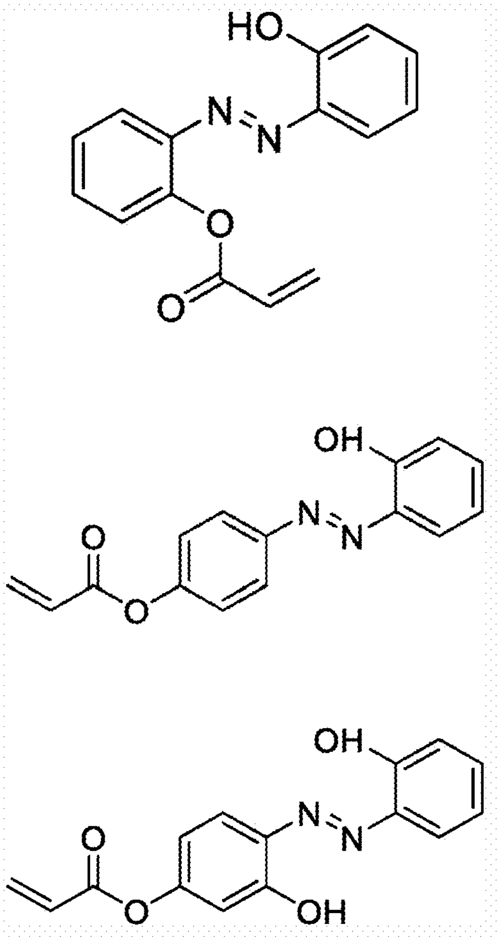

FIG. 22 illustrates a phenolic azobenzene monomers that can be used to make photoactive dental resin materials.

Figure 23:
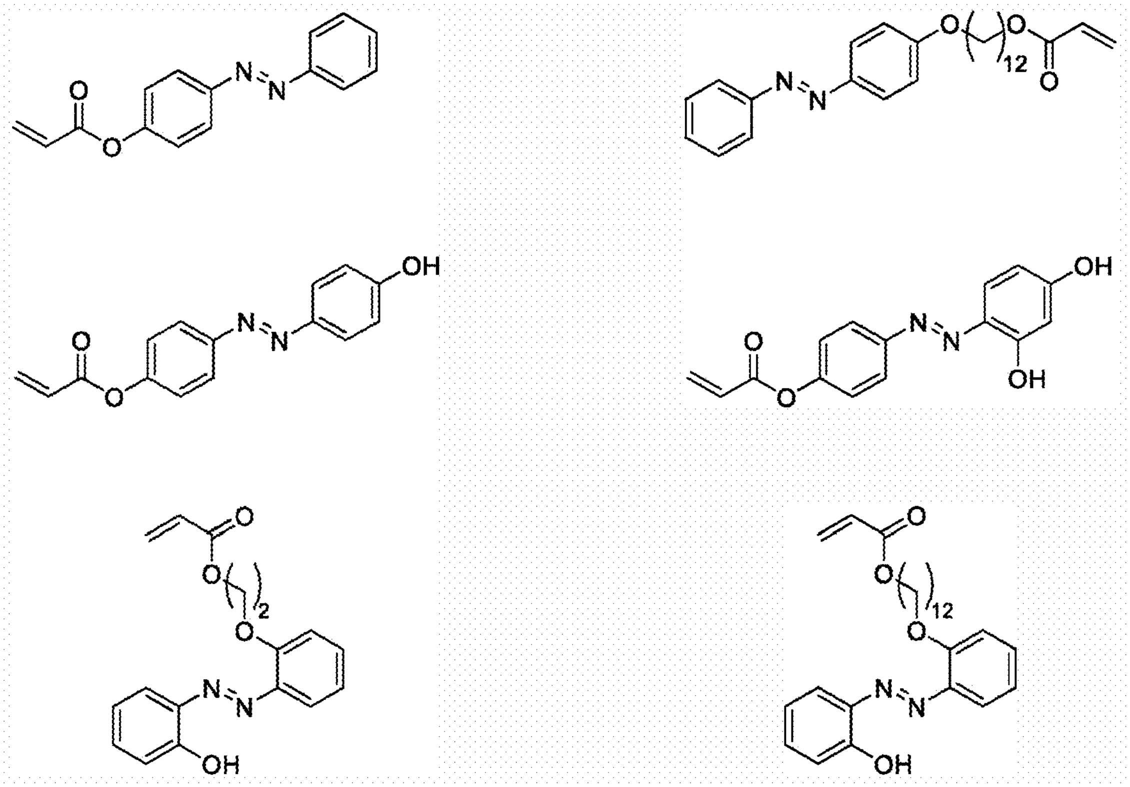

FIG. 23 illustrates azobenzene monomer that can be used to make photactive dental resin materials, wherein said azonbenzene monomers have not been observed to to prevent the growth of an *S. mutans* biofilm grown under sucrose-dependent conditions.

Figure 24:
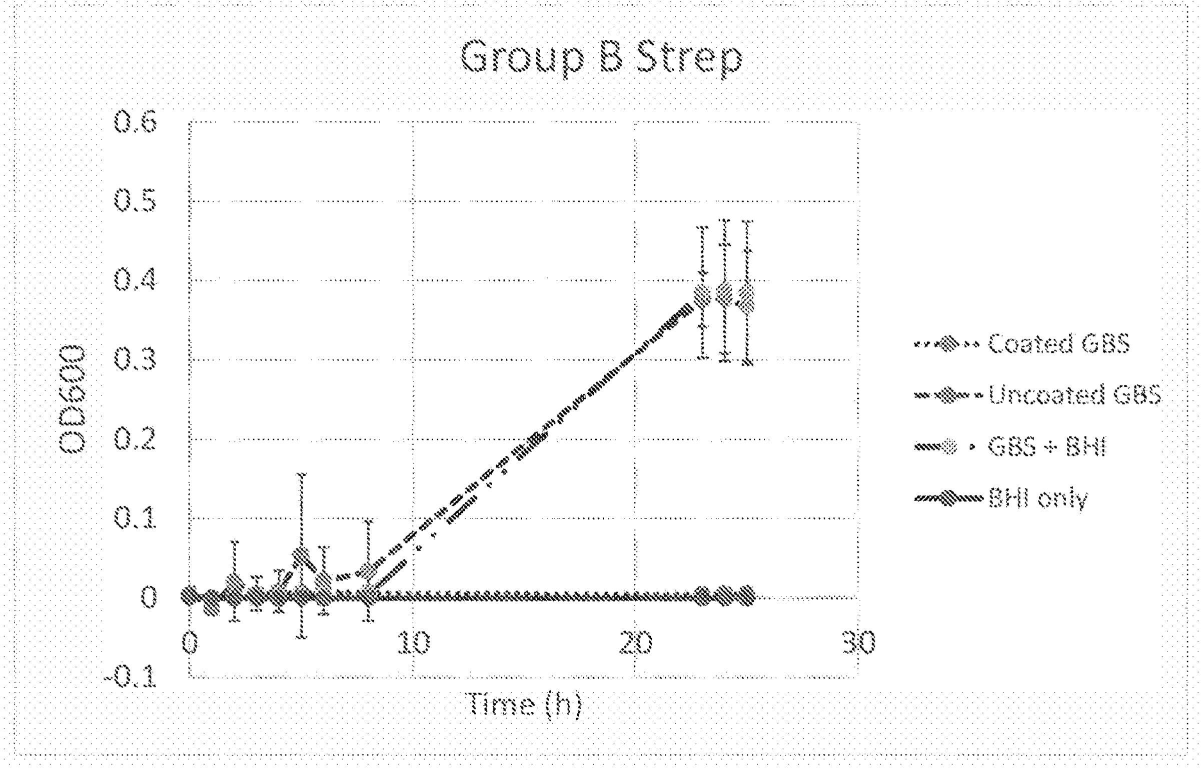

FIG. 24 shows growth curve data of *S. agalactiae* (Group B strep, GBS) using BHI media in 96-well plate in the presence of 50 mg/ML OH-AAZO coated substrates.

Figure 25:
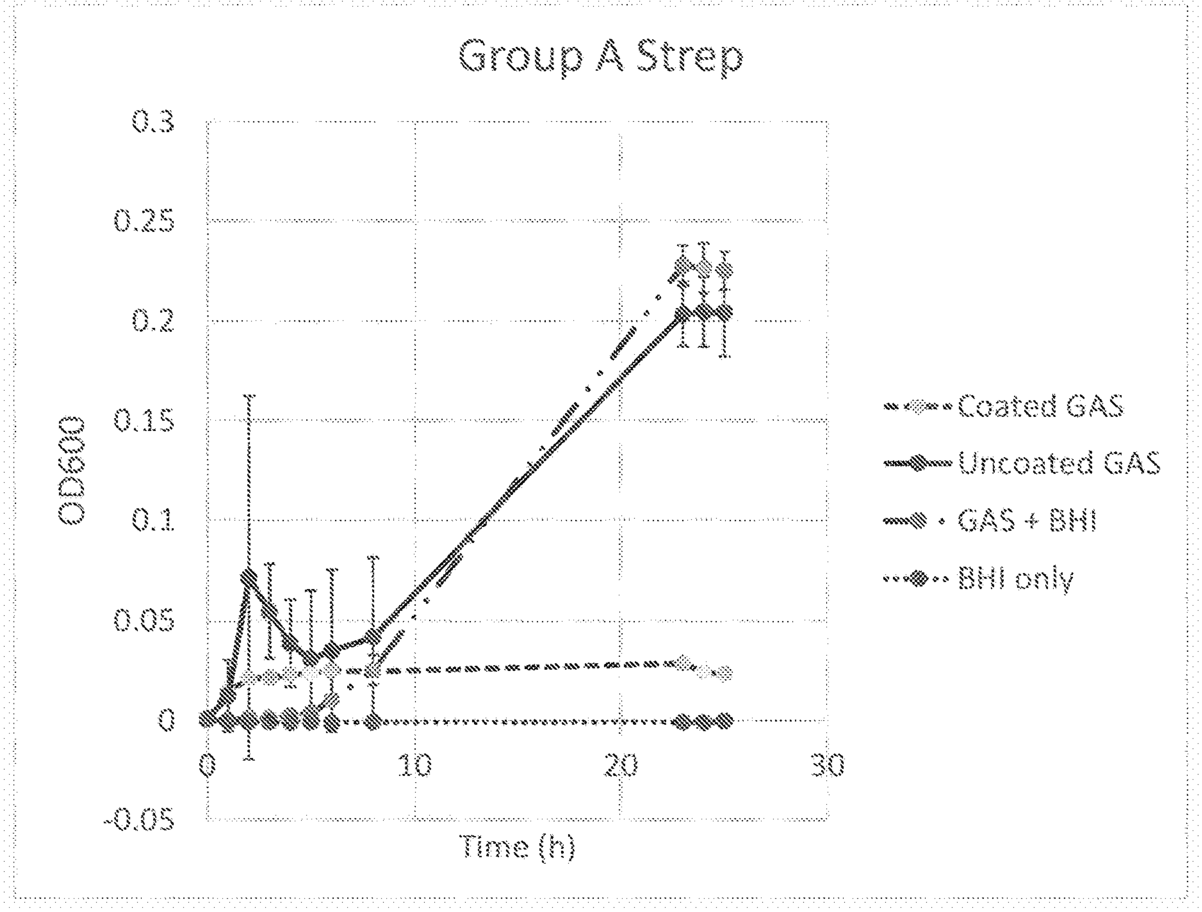

FIG. 25 shows growth curve data of *S. pyogenes* (Group A strep, GAS) using BHI media in 96-well plate in the presence of 50 mg/ML OH-AAZO coated substrates.

Figure 26:
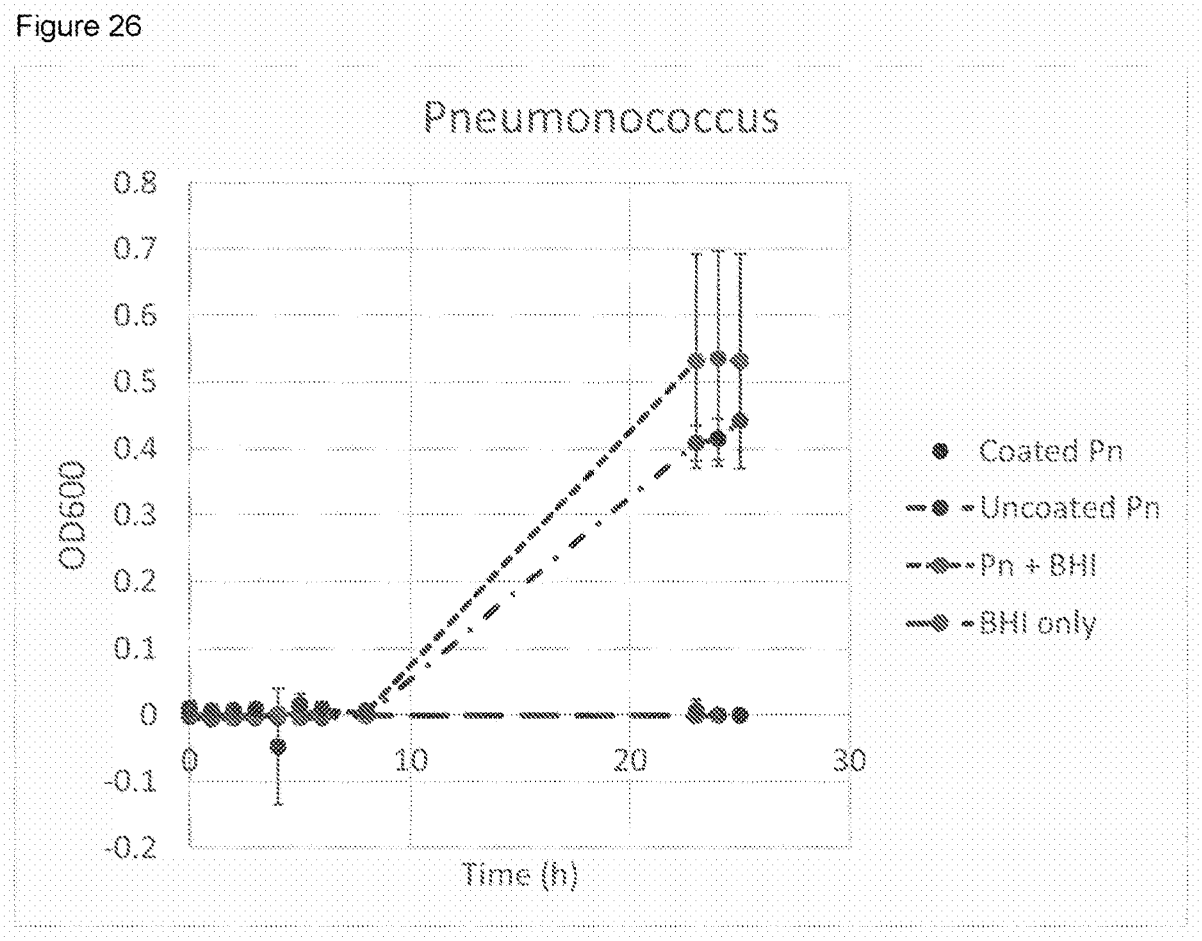

FIG. 26 shows growth curve data of *S. pneumoniae* (Pneumonococcus, Pn) using BHI media in 96-well plate in the presence of 50 mg/ML OH-AAZO coated substrates.

DETAILED DESCRIPTION OF INVENTION

A number of azobenzene monomers have been found to possess antimicrobial properties. The azobenzene monomers include hydroxyl substituent groups that help prevent the formation of microbial biofilms. In one implementation, a phenol-containing azobenzene monomer (OH-AAZO) was shown to prevent the growth of an *S. mutans* biofilm grown under sucrose-dependent conditions. The azobenzene monomers have the capability to act as an antifouling, noninvasive, mechanically stable material for dental restoration. A variety of azobenzene molecules can be used to change the opto-mechanical properties of both single acrylated azomonomers and bulk azopolymer networks.

Figure 1:
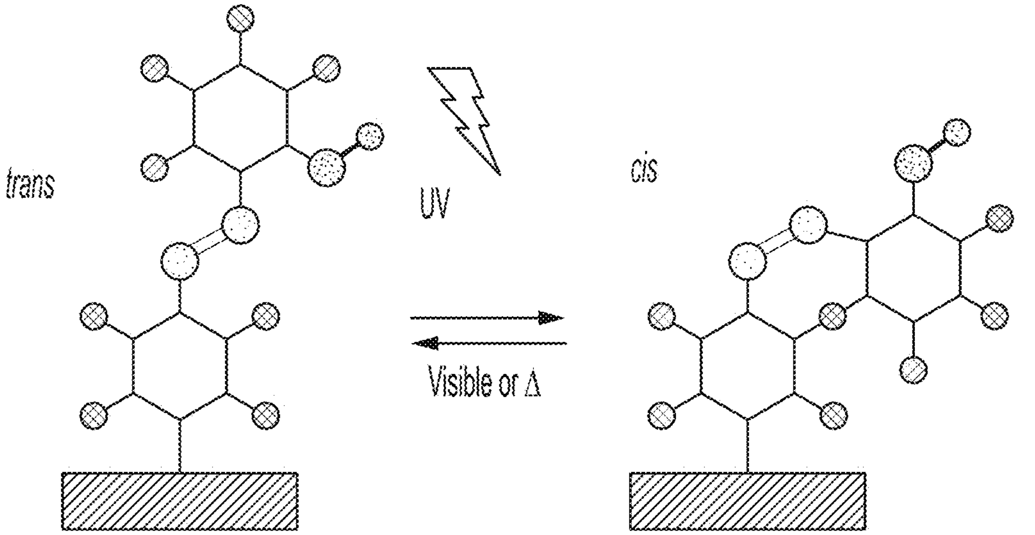
FIG. 1 illustrates one example photoisomerization of a hydroxylated azobenzene that oscillates between trans and cis forms on exposure to UV/Visible light. When irradiated with multiple wavelengths in the visible light spectrum, such as light from a dental lamp (450-470 nm), the azopolymers undergo rapid trans-cis-trans isomerization, generating the photofluidization effect.

Azobenzenes are a class of molecules that create a photofluidization effect (i.e., change their orientation from trans to cis back to trans continuously) upon irradiation by specific wavelengths of light as shown in FIG. 1. When functionalized with a phenolic group, which have antibacterial properties, azobenzenes display antibacterial properties that prevent the *S. mutans* bacteria from colonizing. The combination of the photofluidization effect and the antibacterial activity of the phenolic azobenzenes makes them suitable monomers to incorporate into applications such as a photoactive dental coating that can both kill and repel oral bacterial biofilms.

The removal of oral bacteria from restorative surfaces helps avoid the formation of secondary caries. The rapid photofluidic effect of azobenzene molecules makes it so these compounds can be successfully implemented into Class V oral restorative materials to encourage antifouling and/or antibacterial activity. An acrylated azobenzene monomer can be polymerized as the top layer of these restorative materials so that these materials can, upon exposure to the proper wavelength of light, discourage the colonization and growth of *S. mutans* biofilms via the transient photomechanical motion, which mechanically removes the biofilm from the restoration.

Figure 2:
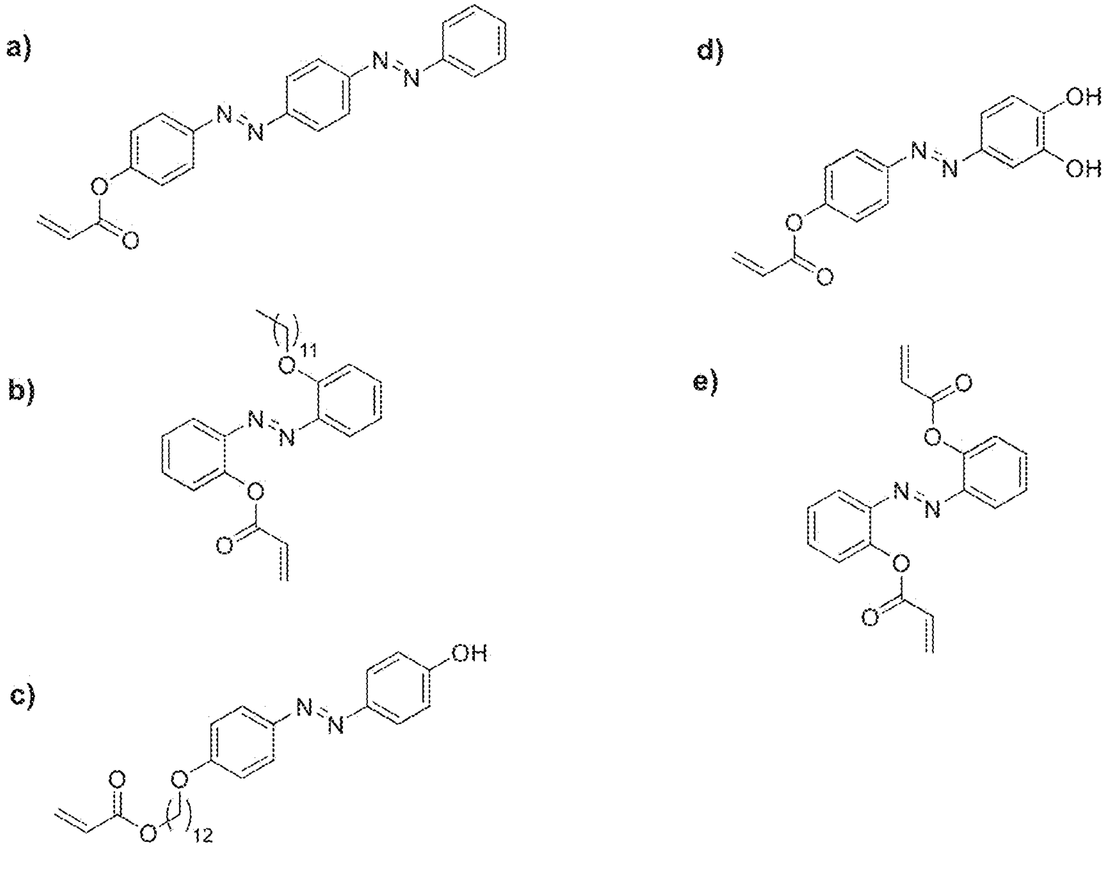
FIG. 2 illustrates some azobenzene monomers that can be used to make photoactive dental resin materials.

Bacterial biofilms can be disrupted via an azobenzene-coated resin substrate. The molecular structure of the azobenzene monomers plays a significant role in the mechanical forces that arise upon photofluidization. Several chemical functional groups can be implemented into azobenzene compounds to have an impact on the mechanical forces of photofluidization. Examples of changes to the chemical structure that may increase the torque forces of the photofluidization include introducing multiple azobenzene groups in series or longer carbon chains such as those shown in FIG. 2*a-c*. Additionally, the presence of additional phenolic groups may improve the disruptive ability of the monomer (FIG. 2*d* and FIG. 22), and may be able to be incorporated into the substrates at a lower concentration for the same antibacterial effect. A diacrylated crosslinking azobenzene monomer (FIG. 2*e*) would impact the mechanical properties of the final coating and its ability to repel a biofilm. The azobenzene compounds can be prepared using established synthetic chemistry methods for either the preparation of azobenzenes or the modification of currently existing azobenzene compounds. NMR can be used to determine the chemical structures of each of these products.

Figure 3:
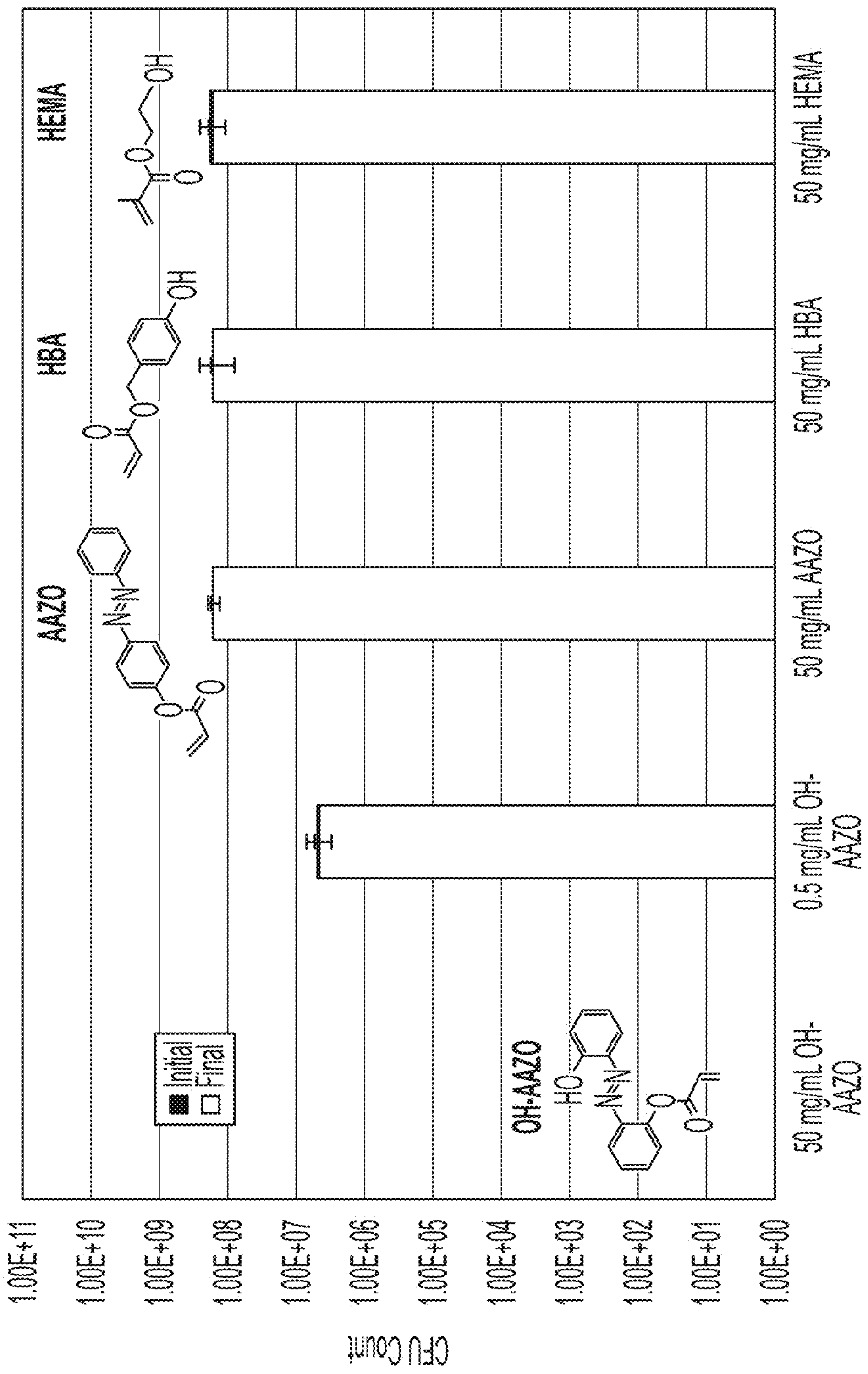
FIG. 3 shows detachment study data for polymeric substrates coated with different monomers. The bar graph indicates the amount of *S. mutans* bacteria removed (by CFU count) in each study. The structures of the monomers coated on the substrates are also included.

Once synthesized, the azobenzene compounds can be incorporated as the outer layer of a methacrylate dental resin material. The formulation of the coating solution of these monomers can also be modified to impact the antibacterial properties. As shown in Example 1, the data suggests that the antibacterial properties of these monomers may be concentration dependent, as substrates prepared using a 0.5 mg/mL solution of OH-AAZO did not result in the same antibacterial effect as the 50 mg/mL coating as shown in FIG. 3. Increasing the concentration of OH-AAZO may aid in the antibacterial activity against different bacterial lines. In addition, combinations of different monomers may produce an even more advantageous combination of antifouling ability (as with OH-AAZO) with biofilm-repellant abilities (as with the monomers in FIG. 2).

The azobenzene monomers' have the ability to remove established biofilms upon light and wash treatments as determined in the Examples below. The BACLIGHT Live/Dead stain can be used to visualize the amount of dead bacteria present on the substrate prior to and after treatment. The individual torque forces per molecule that arise from photofluidization upon irradiation can be calculated using atomic force microscopy.

The adhesive strength (AS), a measure of the energy required to detach the biofilm from the restorative surface, can be determined experimentally as a function of azobenzene coating formulation. This provides a way to characterize the forces of attachment between the biofilm and the azobenzene-functionalized restorative surface.

Combinations of different monomers in the restorative coating can be used to provide an advantageous combination of antifouling ability and biofilm-repellant abilities. The monomers in FIG. 2 can be coated onto resins individually at a concentration of 50 mg/mL in DMF. The monomers can then, optionally, be formulated with OH-AAZO in mass equivalents of 25:75, 50:50, and 75:25 to introduce the antibacterial properties of the monomer.

The mechanical strength values of the monomers can be determined using a modified uniaxial tensile tester (Q800 Dynamic Mechanical Analyzer, TA Instruments) in an environmental chamber designed for biofilm grown on an azobenzene coating, and the method of sample attachment can be modified for AS testing. Biofilms for AS testing can be grown between an azobenzene-coated resin and an uncoated resin to controlled dimensions—e.g., 10 mm×10 mm×20 μm. The biofilm can be removed using a lap-shear 180° peel test, which physically removes the biofilm from the azobenzene coating.

The AS can then be calculated using the following equation:

$$\xi = \frac{W}{A_b \beta'},$$

wherein ξ is the AS (J $m^{-2}$), W is the work required to peel the biofilm from the substrate, A is the total area of the azobenzene coating, and β is the fraction of coating containing biofilm growth.

The azobenzene monomers, formulations, and mechanical characterization methods for detachment can be used to better characterize and understand the forces behind biofilm detachment. In some implementations, azobenzene materials can be prepared including, for example, nanogels, cyclodextrin-containing polymers, which have the ability to disrupt *S. mutans* biofilms.

The presence of OH-AAZO monomers has a demonstrated effect on reducing *S. mutans* biofilm growth in the presence of sucrose, as described above. An MTT assay performed with L929 mouse epithelial cells shows that the OH-AAZO compound is non-cytotoxic as described in Example 3. This suggests that the OH-AAZO compound is biocompatible.

While not wishing to be bound by theory, it is believed that the reason for *S. mutans* biofilm disruption in the presence of OH-AAZO is due to an increase in oxidative stress on the bacterial membrane, leading to lysis and cell death. This is likely due to the increased concentration of reactive oxygen species (ROS) generated by the metabolic pathways of the bacterial cells.

Several assays can be used to detect biomarkers and reaction products from membrane disruption by oxidative stress. Lipid peroxidation is a key indicator of the loss of integrity of the cell membrane. A byproduct of lipid peroxidation is malondialdehyde (MDA), which can react with a thiobarbituric acid (TBARS assay) to form a fluorescent product. By measuring the absorbance of the fluorescent product, the amount of lipid peroxidation (per number of cells) that has occurred from the presence of OH-AAZO can be determined. DNA damage and fragmentation can be another indicator of oxidative stress, and they can be quantified by the use of assays that quantify the amount of 8-OHdG (8-hydroxydeoxyguanosine, a marker of oxidative DNA damage) and fragmented DNA.

The electron transport chain (ETC) of the mitochondria is the primary generator of ROS in bacterial cells, and a decrease in its activity is indicative of cell death. Several assays for biochemical markers involved in the ETC can be used to demonstrate decreased activity. NAD+/NADH and ADP/ATP assays are available from Sigma Aldrich, and an enhancement of each of the ratios can be analyzed for a sample of interest (*S. mutans* grown in the presence of OH-AAZO) relative to a control (*S. mutans* grown on an uncoated sample). An increase in either of these ratios (i.e., an increase in the concentration of NAD+ and ADP) for the OH-AAZO sample would be indicative of higher rates of bacterial necrosis and cell death. The increased presence of other biomarkers involved in the ETC, such as superoxide dismutase and catalase, can suggest an increase in cell death, while a reduced amount of glutathione (GSH) can indicate a more inactive ETC as well.

Confocal microscopy can be used to observe the ratio of live to dead bacteria remaining on the substrates after biofilm growth. Field-emission scanning electron microscopy can be used to visually confirm the damage done by the OH-AAZO to the cell membrane and wall of the *S. mutans*.

Because oxidative stress is strongly influenced by the accessibility and permeability of the phenolic oxidizing species in relation to the bacterial membrane, both a tethered (polymerized) OH-AAZO coating and a free (monomeric) OH-AAZO molecule can be tested in the assays. The free OH-AAZO molecule should more readily diffuse through the membrane than the tethered OH-AAZO, and can be used to identify any limitations in effectiveness in the tethered coating due to the limited mobility of its pendent OH-AAZO groups.

The byproducts of oxidation in the intracellular components of *S. mutans* grown in the presence of OH-AAZO can be observed to confirm that the antibacterial activity of OH-AAZO is due to induced oxidative stress. In addition, the extent ROS compounds are generated resulting from the autooxidation of OH-AAZO can be determined.

It should be appreciated that the azobenzene material can be reacted on any suitable polymeric substrate. In some implementations, the polymeric substrate can be made entirely of polymeric material. In other implementations, the polymer substrate can be a composite material that is made of a combination of polymeric materials and non-polymeric materials.

The polymeric substrate can include any suitable polymeric material. In some implementations, the polymeric substrate can be formed using one or more (meth)acrylate monomers/polymers either alone or in combination with other suitable monomers/polymers. Examples of suitable (meth)acrylate polymers/monomers include methyl methacrylate, polymethylmethacrylate, and the like.

In some implementations, the polymeric substrate is a dental resin-based composite material. Such materials typically include a resin-based oligomer matrix and a filler. The oligomer matrix can be formed from a variety of monomers/polymers including methacrylate monomers/polymers such as methyl methacrylate (MMA), polymethylmethacrylate (PMMA), dimethacrylate monomers such as bisphenol A-glycidyl methacrylate (BISGMA), triethylene glycol dimethacrylate (TEGDMA), urethane dimethacrylate (UDMA), 1,6-Hexanediol dimethacrylate (HDDMA), and the like.

The filler can be included to give the composite greater strength, wear resistance, decreased polymerization shrinkage, improved translucency, fluorescence, and color, and a reduced exothermic reaction during polymerization. In some implementations, the filler is an inorganic material such as glass, ceramic, and/or glass ceramics. Suitable glass fillers materials made of crystalline silica, silicone dioxide, lithium/barium-aluminum glass, and/or borosilicate glass containing zinc/strontium/lithium. Suitable ceramic fillers include materials made of zirconia-silica, zirconium oxide, and the like.

In some implementations, the azobenzene polymers can be used as an antimicrobial coating on pit and fissure dental sealants. Microtensile bond strength (μTBS) results indicated that the strength of the pit and fissure sealant was not compromised with the introduction of the azopolymer coatings (OH-AAZO and/or AAZO). *S. mutans* biofilm growth was significantly reduced with AAZO coatings and absent with OH-AAZO coatings on pit and fissure sealants. Azobenzene coatings can be incorporated into pit and fissure sealants as an anti-bacterial coating to prevent tooth decay.

EXAMPLES

The following examples are provided to further illustrate the disclosed subject matter. They should not be used to constrict or limit the scope of the claims in any way.

Example 1

In this Example, polymeric substrates were prepared and coated with azobenzene monomers to determine their ability to repel *S. mutans* biofilms. The coatings were prepared on a model substrate that was designed to emulate conventional polymethacrylate composite resins used in oral restorative materials.

The polymeric substrates were prepared by mixing 54 wt % methyl methacrylate (MMA), 30 wt % polymethylmethacrylate (PMMA, MW ~35 k), and 16 wt % tetraethylene glycol dimethacrylate (TEGDMA) at 70° C. for 2 hr. After mixing, 1 wt. % azobisisobutyronitrile (AIBN) was added to the formulation as an initiator and mixed.

The mixed formulation was added to circular molds (diameter=6.5 mm) cut from a strip of rubber (thickness=0.9 mm) and pressed between two glass microscope slides. The mold was clamped together and thermally cured at 80° C. for 1.5 hr.

The polymeric substrates were coated as follows. Coating solutions were prepared having the following monomer concentrations (see FIG. 3 for structures of the monomers): 0.5 mg/mL and 50 mg/mL solutions of a phenolic acrylated azobenzene monomer (OH-AAZO), 50 mg/mL acrylated azobenzene monomer (AAZO), 50 mg/mL 4-hydroxyl benzylacrylate (HBA), 50 mg/mL 2-hydroxylethyl methacrylate (HEMA).

The OH-AAZO monomer was evaluated because of its hypothesized greater antibacterial ability and increased potential to disrupt Gram-positive bacteria growth. The AAZO monomer was evaluated due to its previously demonstrated ability to repel a variety of biofilms through trans-cis photoisomerization and/or photofluidization when irradiated with polarized light (the OH-AAZO monomer can also repel biofilms using the same mechanism). Although the AAZO coating could repel a number of biofilms, it could not repel those formed by *S. mutans*. The hydroxyl-containing monomers HBA and HEMA were included as controls.

The coating solutions included the monomer in N,N'-dimethylformamide (DMF) along with 0.5 mg/mL of AIBN and 0.1 mg/mL of Rhodamine B as an indicator dye. Once mixed, 3 μL of each coating solution was pipetted onto one side of the polymeric substrate and spun at 1000 RPM for 1 min followed by spinning at 6000 RPM for 3 s. The coating was cured under a nail lamp (Melody Susie UV Gel Nail Polish Dryer, Model DR-301C) for at least 15 min before repeating the coating procedure on the other side.

The controlled growth of biofilms varied depending on the bacteria strain. In the case of *S. mutans*, a BHI agar plate was streaked with *S. mutans* (ATCC 25175) and allowed to incubate at 37° C. in 5% $CO_2$ for 60 hr to isolate a single bacterial colony. The colony was inoculated in 5 mL of BHI and allowed to incubate statically in the 5% $CO_2$ incubator for 24 hr. The stock solution was diluted 1:50 in a 96-well plate containing the substrates of interest and allowed to incubate in the 5% $CO_2$ incubator for an additional 24 hr.

The detachment study quantified the biofilm grown on each substrate via a series of washes in 1×PBS. The substrate was irradiated using a dental lamp (FlashMax P3 Ortho™, 1900 mW/cm2, wavelength=450-470 nm) on the underside of the vial for a total of ten 3 s irradiations per side. Following the series of washes, the substrate was sonicated for 10 min to remove the residual biofilm on the substrate. The wash solutions were serial diluted, plated, and grown at 37° C. and 5% $CO_2$ to obtain the CFU count.

As shown in FIG. 3, the data for *S. mutans* indicated minimal detachment for the substrates coated with AAZO, HBA, and HEMA. However, no growth at all was observed on the surface of the 50 mg/mL OH-AAZO-coated substrate, even prior to light/wash treatment. This suggests that rather than repelling the *S. mutans* biofilm, the OH-AAZO polymer is affecting the ability of the *S. mutans* to attach and/or grow into a sessile biofilm.

Figure 4:
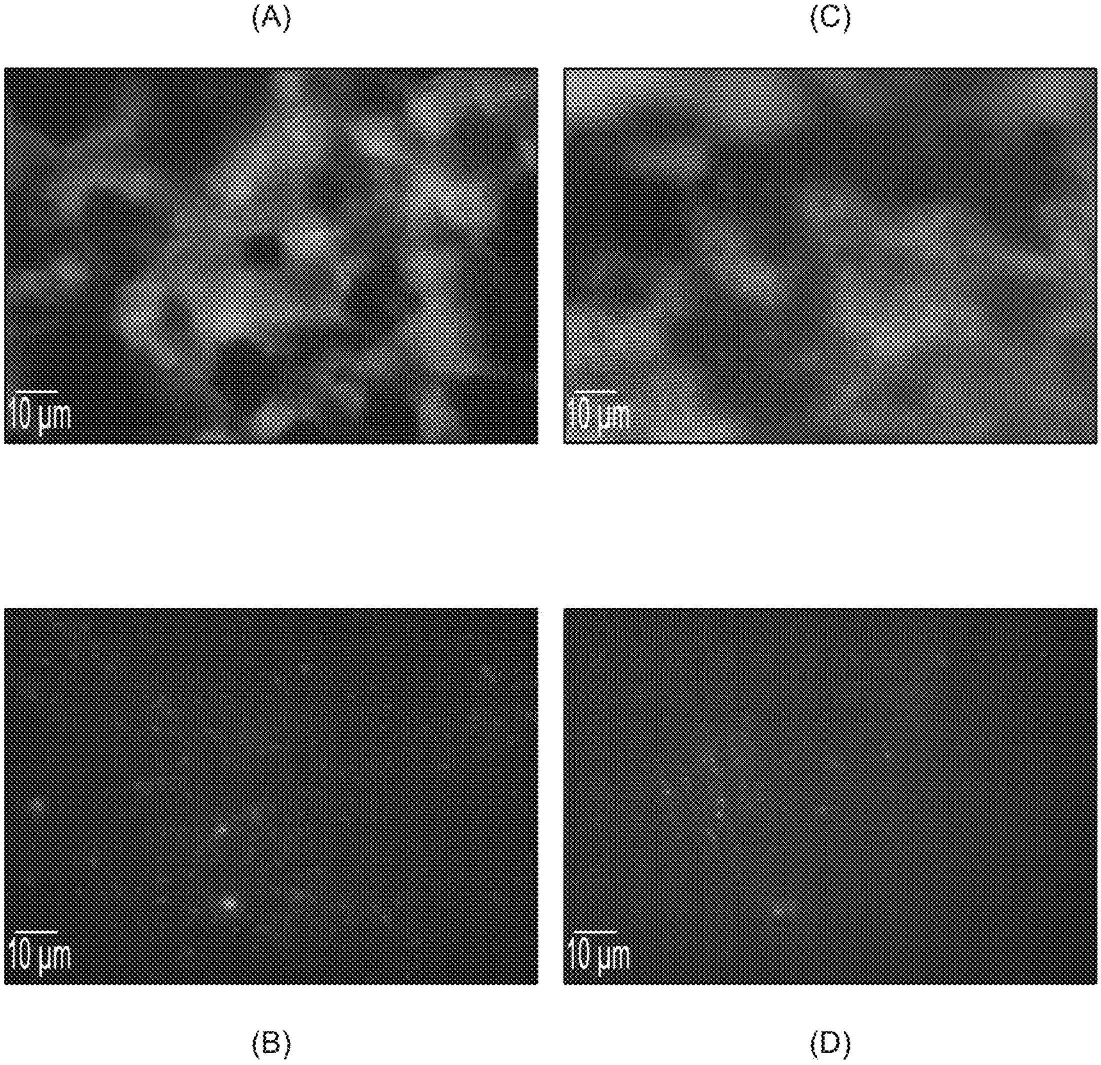
FIG. 4 shows digital microscopy images of an *S. mutans* biofilm grown on two types of coated substrates under sucrose-dependent conditions.

Images collected from a digital microscope (Zeiss Axioplan II microscope, 630×, step size 0.1 μm) after the substrate and bacteria were treated with BACLIGHT Live/Dead stain are included in FIG. 4. The AAZO-coated substrate (FIG. 4*a* and *b*) still contained a robust *S. mutans* biofilm after the treatment, whereas the OH-AAZO-coated substrate (FIG. 4*c* and *d*) had comparatively very little biofilm even prior to treatment.

Example 2

In this Example, detachment of *S. mutans* from a polymeric substrate coated with a 50 mg/mL OH-AAZO solution was evaluated. Four conditions were evaluated. The first is where the polymeric substrate is coated with OH-AAZO and exposed to light to produce a photofluidization effect due to the rapid trans cis isomerization (Azo, light or AL). The second is where the polymeric substrate is coated with OH-AAZO and not exposed to light (Azo, no light or ANL). The third is where the polymeric substrate is not coated with OH-AAZO and is exposed to light (no Azo, light or NAL). The fourth is where the polymeric substrate is not coated with OH-AAZO and is not exposed to light (no Azo, no light or NANL).

Figure 5:
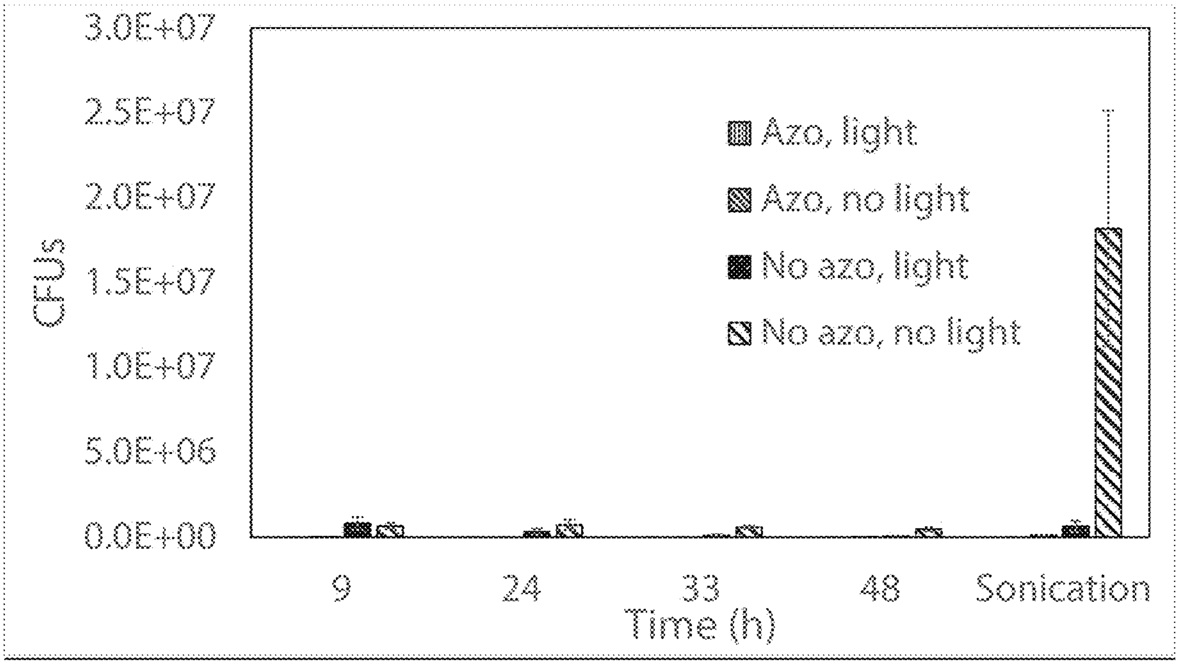
FIG. 5 shows the results of the detachment study in Example 3 (by CFU count) using an OH-AAZO coated substrate.
Figure 6:
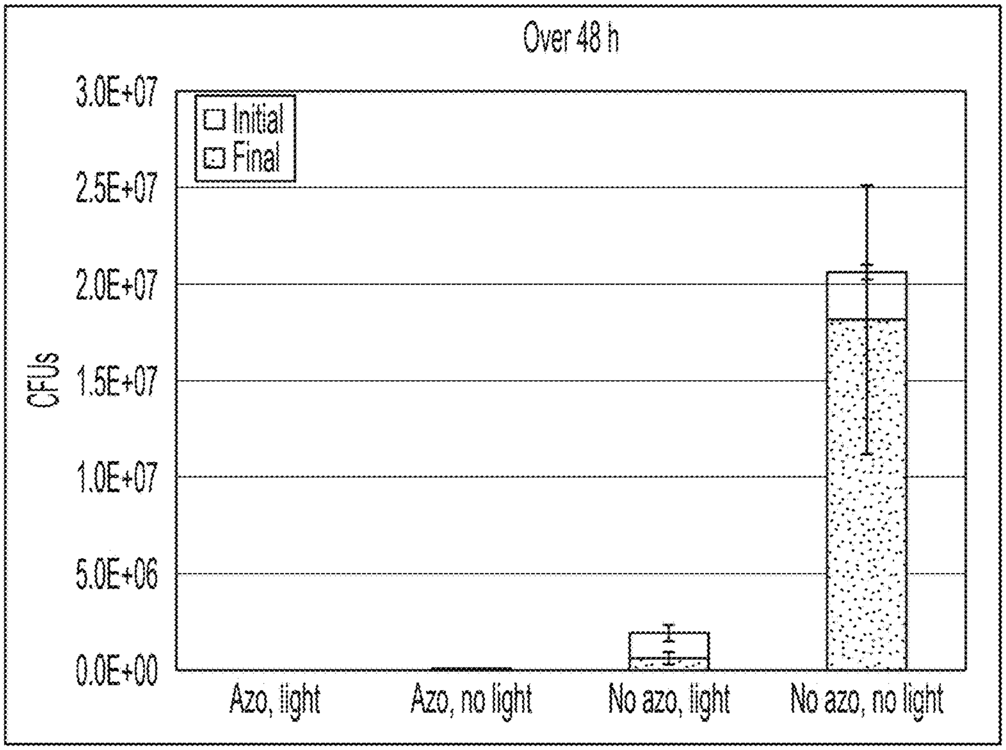
FIG. 6 shows the results of the detachment study in Example 3 using an OH-AAZO coated substrate.
Figure 7:
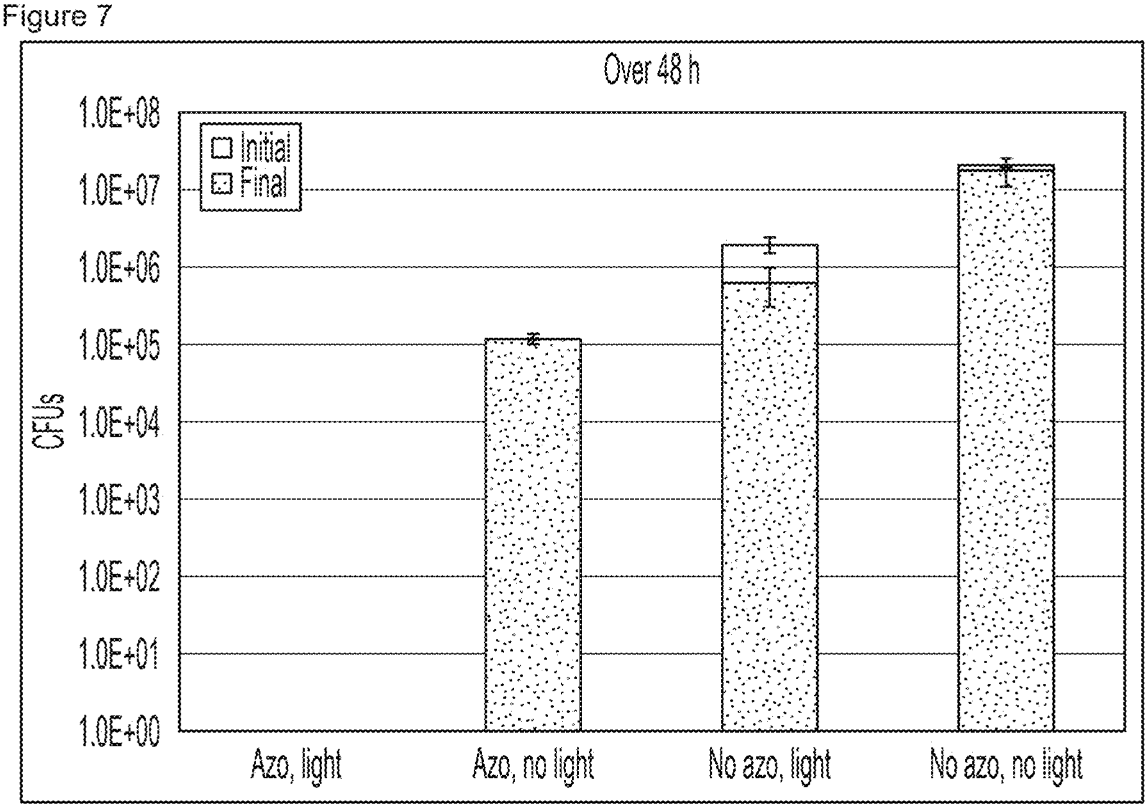
FIG. 7 shows the results in FIG. 6 using a log scale.

The results of the tests are shown in FIG. 5-FIG. 7. The AL sample showed no growth over 48 hr. The ANL sample showed minimal growth for the first 33 hr, but by t=48 hr, there was some minimal biofilm growth. This suggests that the presence of OH-AAZO group inhibits growth even in the absence of light. The NAL had biofilm removed at each treatment, but had less biofilm remaining and overall CFU counts than NANL.

Example 3

In this Example, the cytotoxicity of polymeric substrates coated with 0.5 mg/mL OH-AAZO and 50 mg/mL OH-AAZO in the manner described in Example 1 were tested using L929 mouse epithelial cells. The following six samples were prepared: polymeric substrate coated with 50 mg/mL OH-AAZO, polymeric substrate coated with 0.5 mg/mL OH-AAZO, uncoated polymeric substrate, positive control, negative control, and an empty well. All coatings were spin coated. All samples were run in triplicate.

The cells were grown on substrates for 100 hr with media replacement when necessary. L929 conditions: Passage 3. Initial concentration of cells: 1.67×104 cells/mL.

Methods and assumptions:

Wells containing MTT product were analyzed at 570 nm.

OD570 values were corrected based on OD570 values of wells containing MTT product+other reagents only (no cells).

OD570 values were corrected based on OD570 values of wells containing MTT product+other reagents only (no cells).

Assumes 100% cell death (i.e., 0% cell viability) in these positive control wells.

Negative control (−) wells contained cells grown with no substrate.

Assumes all cell death occurred naturally.

Cell viability was calculated using the following equation:

$$\text{Cell Viability}(\%) = \left(1 - \frac{\text{Mean } OD_{570} \text{ of sample}}{\text{Mean } OD_{570} \text{ of positive control}}\right) \times 100$$

Results: All samples (including negative control) fall within the same margin of error. This suggests that presence of OH-AAZO at any concentration does not contribute significantly to cytotoxicity relative to uncoated sample and negative control (cells grown on their own).

Example 4. Selective Inhibition of *Streptococci* Biofilm Growth via Azobenzene Coatings and Azobenense Subtrates Materials Unless otherwise stated, all compounds and solvents were used as received. 4-hydroxyazobenzene, 2,2'-dihydroxyazobenzene, and azobisisobutyronitrile (AIBN) were acquired from Aldrich. AIBN was recrystallized in methanol prior to use. Hydroxyethyl methacrylate (HEMA), methyl methacrylate (MMA), and polymethyl methacrylate (PMMA, ~35 k) were acquired from Acros Organics. Triethylene glycol dimethacrylate (TEGDMA), 2-hydroxybenzyl alcohol, and acyl chloride were acquired from TCl. N,N-dimethylformamide (DMF), triethylamine, and silica gel were acquired from Fisher. Tetrahydrofuran (THF) was acquired from VWR. Dichloromethane (DCM) was acquired from Millipore. Rhodamine B was acquired from PolySciences.

*S. mutans* (ATCC 25175), *S. aureus* (Herbert, 2010 HG001 or AH2183 or RN1HG), *S. oralis* (ATCC 9811), and *A. actinomycetemcomitans* (ATCC 43718), and *E. coli* (Mysorekar, 2013) were provided from the sources listed. BBL™ Brain heart infusion (BHI) media and Difco™ agar were acquired from BD. Sucrose for cell growth was acquired from MP Biomedicals, LLC. Phosphate-buffered saline (PBS) was acquired from Bioland Scientific. Dulbecco's Modified Eagle Medium (DMEM) media and fetal bovine serum (FBS) was acquired from Fisher. Penicillin-streptomycin and trypsin solution 10× (2.5%) was acquired from Aldrich.

Methods

Synthesis of AAZO

Acrylated azobenzene (AAZO) was synthesized as described by Kehe et al., Optically Responsive, Smart Anti-Bacterial Coatings via the Photofluidization of Azobenzenes. ACS Appl Mater Interfaces (2019) 11(2): 1760-1765. $^1$H NMR: (500 MHz, $CDCl_3$) δ 7.97 (d, 2H), 7.91 (d, 2H), 7.51 (m, 3H), 7.30 (d, 2H), 6.63 (d, 1H), 6.35 (dd, 1H), 6.05 (d, 1H). The outline for the synthesis is set forth in the upper reaction of FIG. 8 according to the a) specifiation of $R_1$, $R_2$, $R_3$, $R_4$, and $R_5$.

Synthesis of OH-AAZO

The phenolic acrylated azobenzene (OH-AAZO) (see b of FIG. 8) was synthesized as described by Kehe et al. with several modifications. Briefly, 2,2'-dihydroxyazobenzene (0.5261 g, 2.46 mmol), trimethylamine (0.41 mL, 2.95 mmol), and 25 mL DCM were combined in a flame-dried Schlenk flask under $N_2$ and stirred for 0.5 h at 0° C. Acyl chloride (0.20 mL, 2.46 mmol) was added dropwise, and the solution was stirred overnight at room temperature. The organic layer was washed with water three times (15 mL per wash) and dried over $MgSO_4$. The crude product was purified via column chromatography using DCM as an eluent ($R_f$=0.77) and yielded OH-AAZO as a red-orange crystal. Yield: 0.41007 g (62%). $^1H$ NMR (500 MHz, $CDCl_3$) δ 12.75 (1H, s), 7.97 (2H, d), 7.55 (1H, t), 7.38 (3H, m), 7.09 (2H, m), 6.75 (1H, d), 6.46 (1H, dd), 6.16 (1 H, d). The outline for the synthesis is set forth in the upper reaction of FIG. 8 according to the b) specifiation of $R_1$, $R_2$, $R_3$, $R_4$, and $R_5$.

Synthesis of 4-Hydroxybenzyl Acrylate (HBA) Control Monomer 4-hydroxylbenzyl acrylate (HBA) was prepared by the method described previously. Seo et al., *Significant Performance Enhancement of Polymer Resins by Bioinspired Dynamic Bonding*., Adv Mater. (2019), 29(39):1-9. Briefly, 4-hydroxybenzyl alcohol (1.2637 g, 10.2 mmol) was combined with trimethylamine (1.70 mL, 12.2 mmol) in 12 mL THF in a flame-dried Schlenk flask under $N_2$. The solution was mixed for 0.5 h at room temperature and then cooled to 0° C. Acyl chloride (0.82 mL, 10.2 mmol) was added slowly dropwise and allowed to stir for 24 h. The THF was removed via rotovap, and the residue was extracted with a 20 mL DCM wash twice with 0.1 M HCl, then twice with DI water. The DCM layer was run through a silica plug to yield an opaque slightly yellow oil. Yield: 0.8132 g (45%). $^1H$ NMR (500 MHz, DMSO-$d_6$) δ 9.56 (1H, s), 7.47 (2H, d), 7.21 (2H, d), 6.76 (1H, d), 6.52 (1H, d), 6.37 (2H, m), 6.16 (2H, m), 5.99 (1H, dd). The outline for the synthesis is set forth in the lower reaction of FIG. 8.

Making Base Polymers

Formulations of MMA:TEGDMA:PMMA base polymers were prepared using 56 wt. % methyl methacrylate (MMA), 30 wt. % tetraethylene glycol dimethacrylate (TEGDMA), and 14 wt. % polymethyl methacrylate (PMMA, MW ~35 k). The components were stirred at 70° C. for 2 h. 1 wt. % AIBN (relative to the total mass of the mixture) was added and the formulation was stirred for an additional 0.5 h.

Formulations of bisGMA-TEGDMA were prepared using 70 wt. % bisphenol A-glycidyl methacrylate (bisGMA) and 30 wt. % TEGDMA. The components were stirred at room temperature until fully dissolved. Camphorquinone (0.5 wt. %) and ethyl 4-dimethyl amine benzoate (0.5 wt. %) were added to the formulations for the uncoated bisGMA-TEGDMA substrates and stirred at room temperature until dissolved.

Circular holes (d=5.5 mm) were punched in a rubber spacer (0.8 mm thickness) placed on a glass microscope slide. Both formulations were pipetted into each hole and sandwiched between an additional glass slide with binder clips. The substrates were cured at 80° C. for 1.5 h. Conversion rates were observed via FT-IR for the integration under the acrylate peak (6250-6096 $cm^{-1}$).

OH-AAZO Coatings on Subtrates and Bulk OH-AAZO Substrates

Coating formulations of OH-AAZO were prepared in THF, all others were prepared in DMF. The THF volume was kept constant (1 mL) and the mass of OH-AAZO monomer was varied to attain the desired concentration. In addition to the OH-AAZO monomer, the coating also consisted of AIBN (2 wt. % relative to the mass of the monomer), and Rhodamine B (0.2 wt. % relative to the mass of the monomer).

Once cured, the MMA:TEGDMA:PMMA base polymers were placed into a mount on a square glass microscope slide. 3 μL of the coating formulation was added via pipette to one side of the substrate and spin coated (1000 rpm for 1 min, 6000 rpm for 3 min), then the process was repeated on the other side. Once both sides were coated, they were placed in an oven for 3 h at 100° C., then under vacuum for an additional 0.5 h.

Bulk OH-AAZO formulations were prepared using the acrylic base polymer method with the addition of the appropriate weight percentage of OH-AAZO (relative to the total mass of the formulation) and AIBN (rather than camphorquinone/amine, 2 wt. %). The components were stirred at room temperature until completely dissolved. The formulations were pipetted into the rubber spacer and cured for 1 h at 100° C. Conversion rates were observed via FT-IR.

Extraction Protocol

Figure 9:
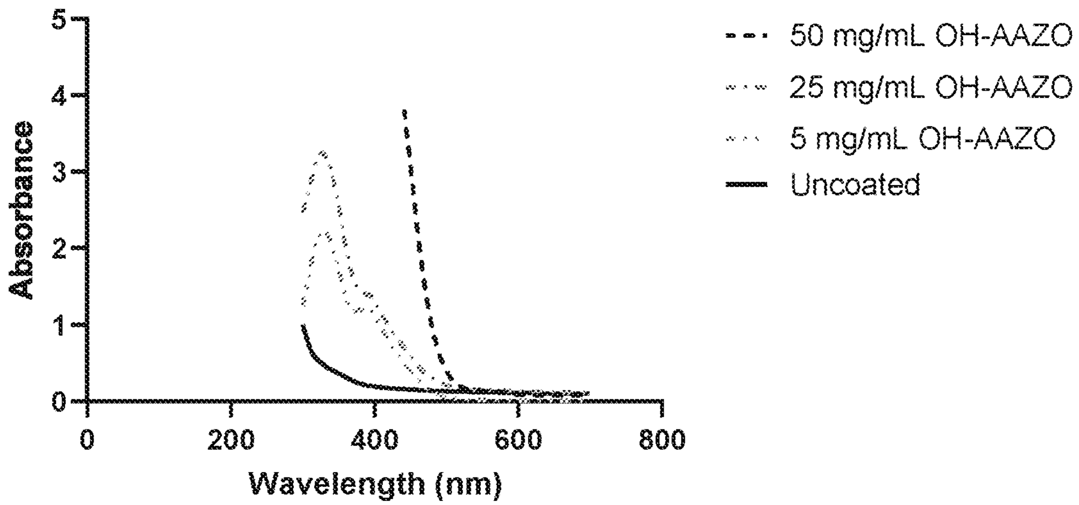
FIG. 9 shows cell toxicity reults for UV-Vis spectra of OH-AAZO coatings at different concentrations (plus an uncoated control substrate) immediately following thermal curing and aqueous extraction.

Following curing, residual monomer was aqueously extracted by autoclaving (20 psi, 128° C.) for 1 h in MilliQ water (approx. 5 mL water per substrate). The MilliQ water was replaced with fresh water (approx. 5 mL water per substrate) and placed in an 80° C. oven for 2 h. The substrates were blotted dry and analyzed via UV-Vis spectroscopy to confirm the relative amount of the coating (FIG. 9). All coated and bulk substrates were autoclaved prior to their use with both mammalian and bacterial cells.

Cytotoxicity

Figure 10:
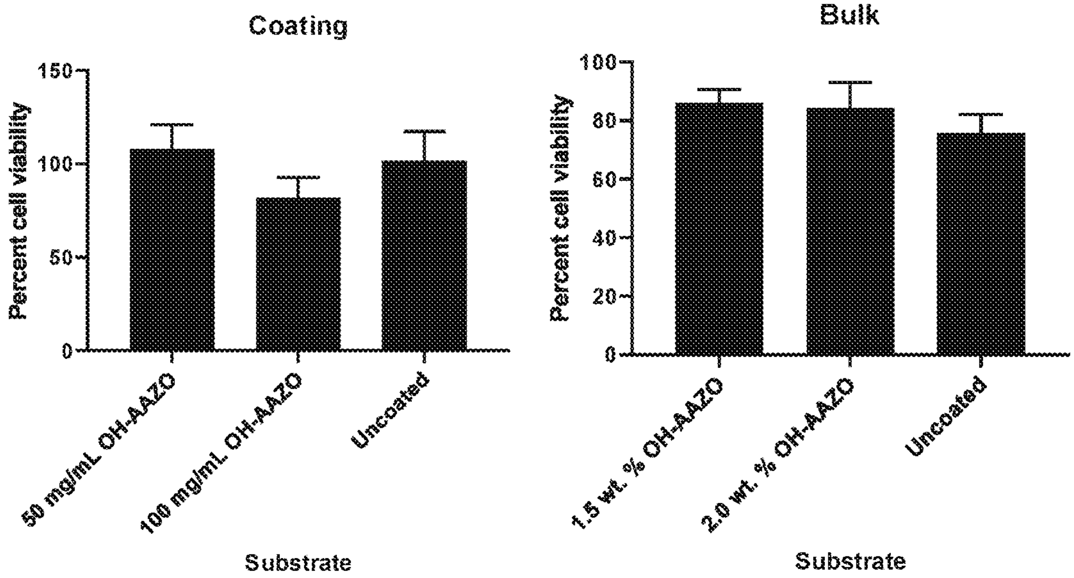
FIG. 10 is shows cell cytotoxicity results for L929 mouse epithelial cells on (A) 50 mg/mL and 100 mg/mL OH-AAZO coated substrates compared to an uncoated substreate and (B) 1.5 wt % and 2.0 wt % bulk OH-AAZO substrates compared to substrate not comprising OH-AAZO in the bulk. All values were normalized to a positive control (i.e., cells grown in the absence of a substrate).
Figure 11:
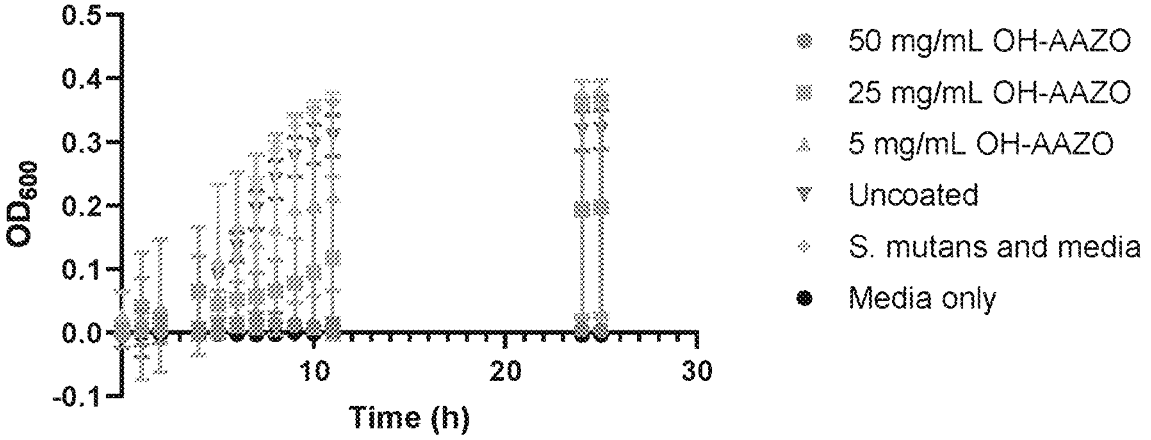
FIG. 11 shows growth curve data of *S. mutans* in a 96-well plate in the presence of (A) OH-AAZO coated substrates and (B) bulk OH-AAZO substrates at different concentrations.
Figure 11:
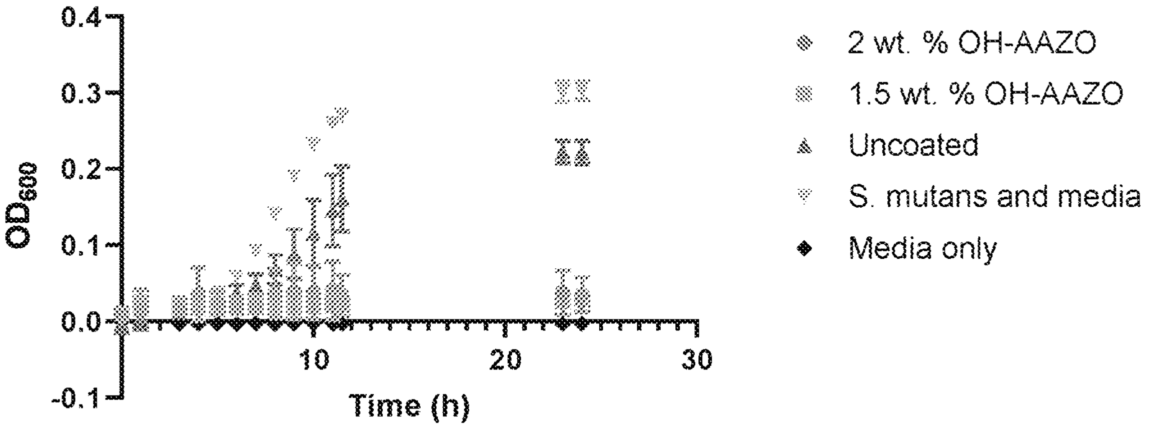

Cytotoxicity studies were performed as described previously. Riss et al., *Cell Viability Assays*, (Promega). Briefly, L929 mouse epithelial cells were suspended in cell culture media (DMEM, 10% FBS, 1% penicillin streptomycin) to a final concentration of $1.06 \times 10^5$ cells/mL. 1 mL of the suspension was added to each well in a 24-well plate containing the substrates and allowed to grow to confluence. Cell growth was monitored via a phase contrast inverted microscope (Leica, WLD MPS32, Germany). Once confluent, the media was aspirated off, and 500 μL of a 1 mg/mL solution of MTT reagent in DMEM media was added to each well. The plate was incubated for 4 h, and 500 μL of 20% SDS in 50% DMF was added to each well containing the MTT reagent. The plate was incubated for an additional 24 h, then removed and analyzed by an absorbance reading at λ=570 nm (FIG. 10).

Culturing *S. mutans*

*S. mutans* biofilms were grown from a 24 h BHI liquid culture inoculated with an isolated *S. mutans* colony. The liquid culture was diluted 1:50 in BHI media containing 1 wt. % sucrose in each well in a 96-well plate containing a substrate of interest. The plate was incubated in the dark at 37° C. and 5% $CO_2$ for the necessary amount of time (t=24 h, 48 h, 72 h, depending on the experiment).

Culturing *S. oralis*, *A. actinomycetemcomitans*, *S. aureus*, and *E. coli* Bacterial Strains

*S. oralis* and *A. actinomycetemcomitans* were streaked on a BHI agar plate and incubated at 37° C. and 5% $CO_2$ for 48 h. An isolated colony was inoculated in 5 mL BHI media for 12 h under the same incubation conditions, followed by a 1:10 dilution in BHI media in a 96-well plate containing the substrates of interest. *S. oralis* biofilms were allowed to grow for 9 h, and *A. actinomycetemcomitans* biofilms were allowed to grow for 30 h.

Methicillin-susceptible *S. aureus* biofilms were grown from a 20 h BHI liquid culture inoculated with an *S. aureus* colony. The liquid culture was diluted $10^3$ to a stock solution in BHI, then diluted 1:10 in BHI media containing 0.4 wt. % glucose in a 96-well plate. The plate was incubated in the dark at 37 ° C. for 24 h.

*E. coli* biofilms were grown from a 20 h BHI inoculated with an *E. coli* colony. The liquid culture was diluted $10^3$ to a stock solution in BHI, then diluted 1:10 in BHI media in a 96-well plate. The plate was incubated in the dark at 37° C. for 24 h.

Culturing *S. adalactieae*, *S. pyogenes*, and *S. pneumaoniae*

A single bacterial colony was inoculated in 4 mL BHI media. The colony was grown to mid-log phase (to approximately OD600=0.4), statically at 37° C., which for was approximately 4 hours for the *S. agalactiae* GBS, approximately 11 hours for the *S. pyogenes* GAS, and approximately 6 hours for the *S. pneumaoniae*. They were diluted 1:5 in 80% glycerol (in water) solution (4 parts culture, 1 part glycerol, for a final glycerol concentration of 16%). In a 96-well plate, each was diluted to 1:100 resulting in a final concentration of $1\times10^6$ CFU/mL and grown at 37° C. with 5% $CO_2$.

Growth Studies

Following biofilm growth in the 96-well plate, the substrates were aseptically removed from the 96-well plate and placed in a vial containing 5 mL of 1× PBS solution. The vials were sonicated in a water bath for 10 min at 45° C., and the wells that previously contained the substrates were briefly sonicated using a probe sonicator (3 W RMS output) for 10 s per well. 200 μL aliquots of the sonicated PBS solution were placed in a 96-well plate and diluted 1:10 in each subsequent row. 20 μL aliquots of the sonicated media wells were placed in a 96-well plate containing 180 μL of PBS solution and diluted 1:10 in each subsequent row. Each column was then plated at a volume of 10 μL on a BHI agar plate in triplicate. The plates were then incubated at 37° C. and 5% $CO_2$ for 48 h. The CFUs on each plate were counted in order to quantify the amount of biofilm remaining on the surface of the substrate and the bacteria remaining in the media after the removal of the substrate using the following equations:

$$CFU_{substrate} = \frac{CFU_{spot}}{10\ \mu L} \times 5000\ \mu L \times 10^{Row-1} \quad \text{Equation S1}$$

$$CFU_{media} = \frac{CFU_{spot}}{10\ \mu L} \times 200\ \mu L \times 10^{Row} \quad \text{Equation S2}$$

Where $CFU_{substrate}$ and $CFU_{media}$ are the total CFU counts on the substrate and in the media well, respectively. $CFU_{spot}$ is the number of CFUs counted in a single spot on the plate, and Row is the corresponding numerical row number for the spot counted.

Microscopy

Microscope images were obtained using a Zeiss digital microscope at 6300× magnification using the FITC and CY3 channels. Following biofilm growth, the substrates were placed in a solution of live-dead stains (Invitrogen BacLight™) containing 1.5 μL Component A (SYTO® 9, green fluorescent nucleic acid stain) and 1.5 μL Component B (propidium iodide, red fluorescent nucleic acid stain) in 200 μL of sterile water. The substrates were soaked for 3 min, then gently washed in sterile water for 10 s, dried, and fixed to a glass slide prior to imaging.

Membrane Potential Assay

Membrane potential assays were performed as described by Wu et al. with minor modifications. Wu et al., *Antibacterial activity and membrane-disruptive mechanism of* 3-*p*-*trans-coumaroyl*-2-*hydroxyquinic acid, a novel phenolic compound from pine needles of Cedrus deodara, against Staphylococcus aureus*, Molecules (2016), 21(8):1-12. *S. mutans* bacteria grown for 24 h in BHI broth were inoculated in a 96-well plate as described above. The plate was incubated for 8 h at 37° C. and 5% $CO_2$. 2 μL of 0.1 mg/mL DIBAC4 (3) solution in DMSO was added to each well. The plate was then incubated in the dark overnight. The fluorescence reading was taken in a plate reader at $\lambda_{excitation}$=492 nm and $\lambda_{emission}$=515 nm. Fluorescence values in bacteria-containing wells were normalized against fluorescence values containing the same substrate but no bacteria.

Results

Concentration Dependence of OH-AAZO Antibacterial Effect Against *S. mutans*

Figure 16:
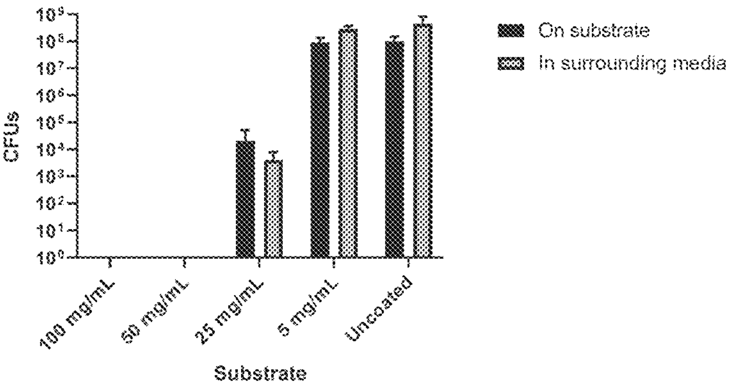
FIG. 16 contains detachment study results of *S. mutans* biofilms as a function of OH-AAZO concentration within the coatings (FIG. 16 (A)) (all n≥3). Microscope images (630× magnification) of *S. mutans* bacteria growing on both uncoated and coated substrates (the (B) and (C) images, respectively).
Figure 16:
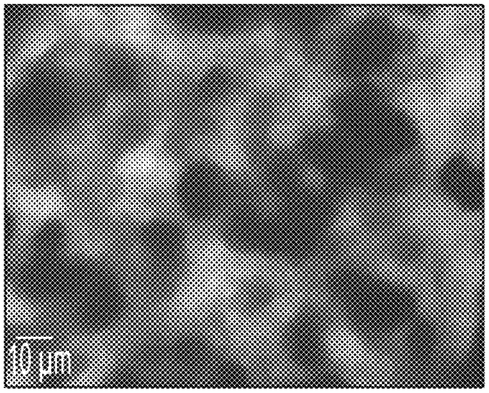
Figure 16:
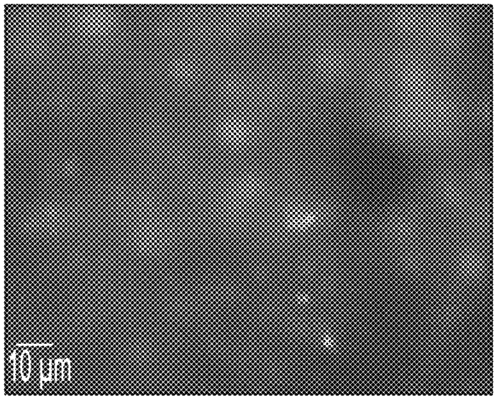

FIG. 16 (A) compares OH-AAZO coatings prepared from coating solution concentrations of 100 mg/mL, 50 mg/mL, 25 mg/mL, and 5 mg/mL in THF. After 24 h of *S. mutans* biofilm growth, the 100 mg/mL and the 50 mg/mL OH-AAZO substrates had no observable CFUs detected on their surfaces. At 25 mg/mL OH-AAZO, there was a 4-log reduction in CFUs for the *S. mutans* biofilm relative to the uncoated control. At 5 mg/mL OH-AAZO, there was no significant difference in CFUs between the coated and uncoated substrates (approximately $1.0\times10^8$ CFUs for both). In the case of the uncoated control, 5 mg/ml, and 25 mg/ml coated substrates, the concentration of bacterial biofilms growing on the surface of the substrates and the surrounding media was comparable. However, when complete biofilm inhibition was observed on the substrates, as in the case of the 50 mg/ml and 100 mg/ml coated substrates, bacterial growth in the surrounding media was absent as well. Because the substrates and surrounding media reached complete sterility at concentrations at or above 50 mg/mL OH-AAZO, it was selected for all subsequent studies unless stated otherwise.

Microscopic images (Zeiss Axioplane II digital microscope) of the coated OH-AAZO coatings confirmed visually the prevention of *S. mutans* biofilm growth. Following 24 h of biofilm growth, the substrates were stained with BacLight™ live-dead stains and imaged using the appropriate fluorescence channels, wherein the coated substrate (FIG. 16(C)) contained high amounts of dead bacteria (lighter) and little to no live bacteria (darker) when compared to the uncoated control substrate (FIG. 16(B)).

Figure 20:
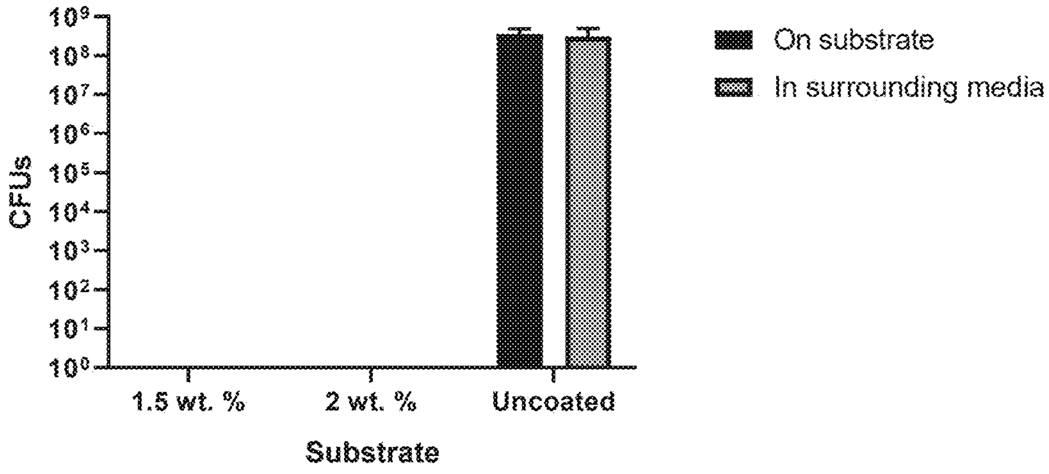
FIG. 20 contains detachment study results of *S. mutans* biofilms on bulk bisGMA:TEGDMA substrates (FIG. 20(A) (all n≥3).
Figure 20:
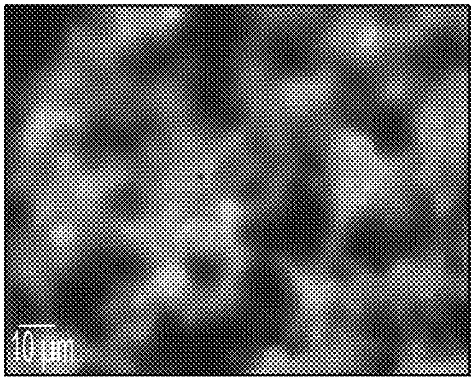
Figure 20:
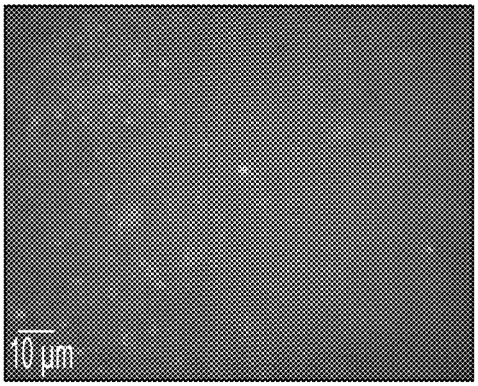
Figure 20:
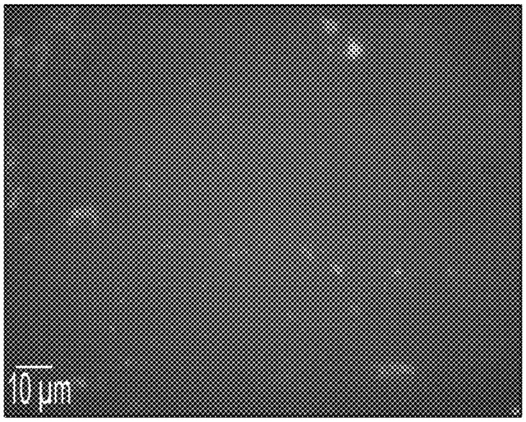

FIG. 20 (A) compares OH-AAZO substrates from 1.5 wt. % and 2 wt. % OH-AAZO bulk substrates to an uncoated subrated. As shown in FIG. 20(A), after 24 h of *S. mutans* biofilm growth, the 1.5 wt. % and 2 wt. % OH-AAZO bulk substrates had no observable CFUs detected on their surfaces and the surrounding media. Microscopic images (Zeiss Axioplane II digital microscope) of the coated OH-AAZO coatings confirmed visually the prevention of *S. mutans* biofilm growth. Following 24 h of biofilm growth, the substrates were stained with BacLight™ live-dead stains and imaged using the appropriate fluorescence channels, wherein a OH-AAZO bulk substrates (FIG. 20(C) and (D), 1.5% and 2% OH-AAZO, respectively) contained high amounts of dead bacteria (lighter) and little to no live bacteria (darker) when compared to the uncoated control substrate (FIG. 20(B)).

Cytocompatibility

Cytotoxicity studies (ISO9993 protocol) confirmed that the 50 mg/mL OH-AAZO substrates were cytocompatible with L929 cells (FIG. 9).

Antibacterial Effect Against Other Bacterial Pathogens

Figure 17:
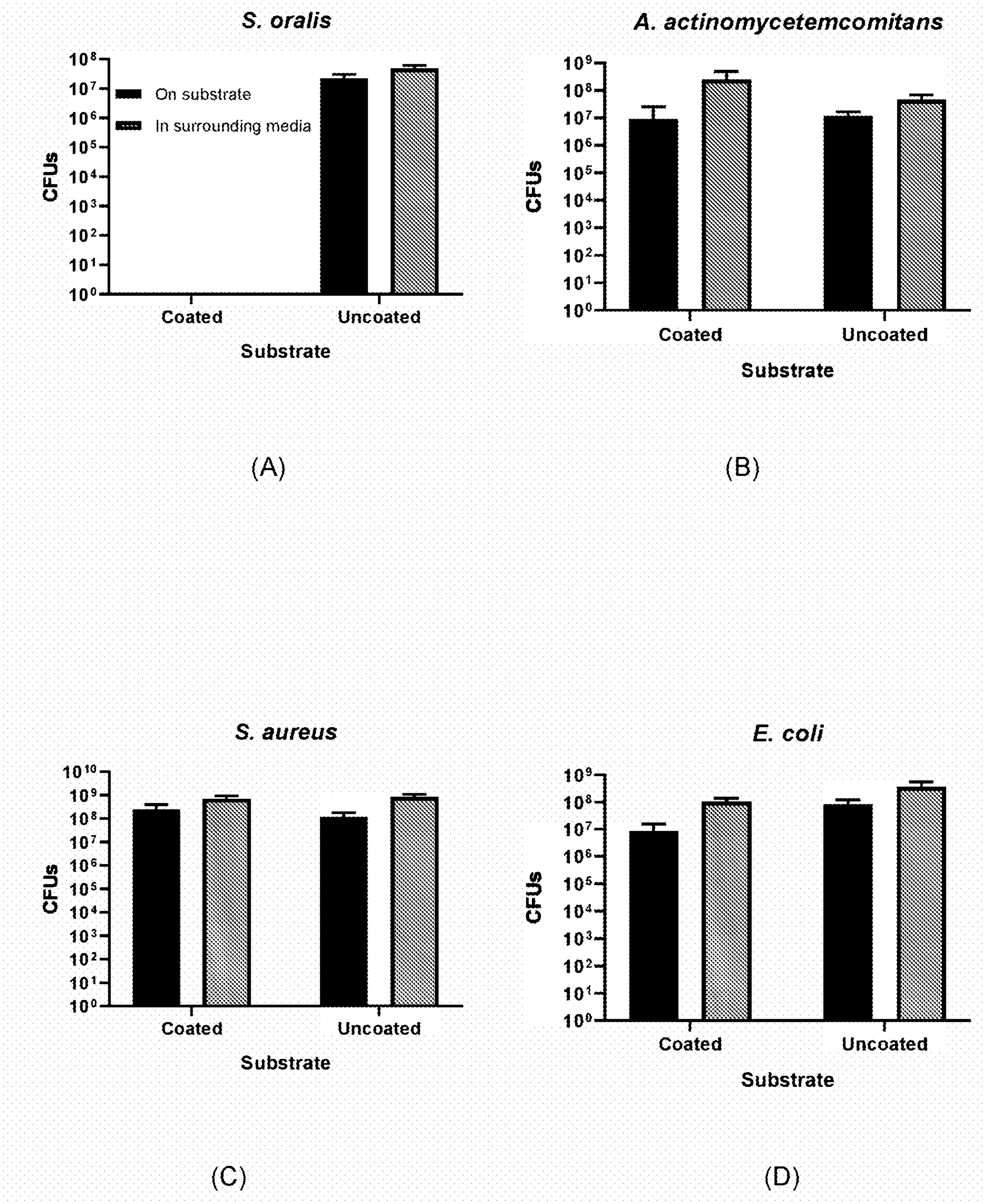
FIG. 17 are graphs showing the selective inhibition of bacterial biofilms of *S. oralis* (FIG. 17(A), *A. actinomycetemcomitans* (FIG. 17(B)), *S. aureus* (FIG. 17(C)), and *E. coli* (FIG. 17(D)) on OH-AAZO coated and uncoated substrates.

*Streptococcus oralis* (*S. oralis*), *Aggregatibacter actinomycetemcomitans* (*A. actinomycetemcomitans*), *Staphylococcus aureus* (*S. aureus*), and *Escherichia coli* (*E. coli*) biofilms were grown on the OH-AAZO substrates over a 24 h time-period. As seen in FIG. 17, *S. oralis* did not grow on the coated substrate nor in the media over this time. However, there was no discernable antibacterial effect or reduction in CFUs for the *A. actinomycetemcomitans, S. aureus*, or *E. coli* biofilms, indicating that the OH-AAZO can potentially selectively target *Streptococci* bacteria.

The effectiveness against *Streptococci* bacteria was confirmed with testing of *Streptococcus agalactiade* (*S. agalactiae*), *Streptococcus pyogenes* (*S. pyogenes*), and *Streptococcus pneumoniae* (*S. pneumoniae*) biofilms were grown on the OH-AAZO substrates over a 24 h time-period. As seen in FIGS. 24-26, *S. agalactiae, S. pyogenes*, and *S. pneumoniae*, respectively, did not grow on the coated substrate nor in the media over this time.

Kill Curve Kinetic Study

Figure 13:
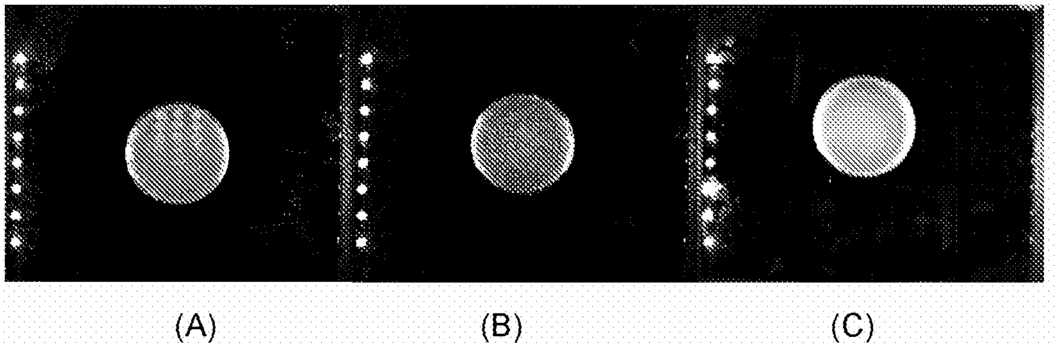
FIG. 13 are images from a complete plating of media of *S. mutans* in contact with OH-AAZO-coated substrates at different timepoints following seeding. The media sampled shown in FIG. 13 (A) at t=0 h was serial diluted as described in Example 4 (below) and gave a total CFU count of $(8.0\pm3.2)\times10^6$ CFUs. The media sampled shown in FIG. 13 (B) at t=4 h was streaked across the entire plate and gave a total CFU count of 8 CFUs. The media sampled shown in FIG. 13 (C) at t=24 h was streaked across the entire plate and gave a total CFU count of 0 CFUs.

We sampled aliquots of the media containing *S. mutans* surrounding the OH-AAZO substrate at different time points (FIG. 4). At t=0, *S. mutans* colonies ($1\times10^6$ CFUs) were introduced to the OH-AAZO coated substrate. At t=4 h, the CFU count in the well was reduced 2-log, and by t=6 h, the CFU count had reduced to zero. In a separate study, the entire volume of the media in the well plated onto a BHI agar plate yielded no discernable CFU counts, further confirming that the OH-AAZO coating was successful in eliminating the *S. mutans* colonies from the surrounding media (FIG. 13).

Structure-Function Relationship

Figure 14:
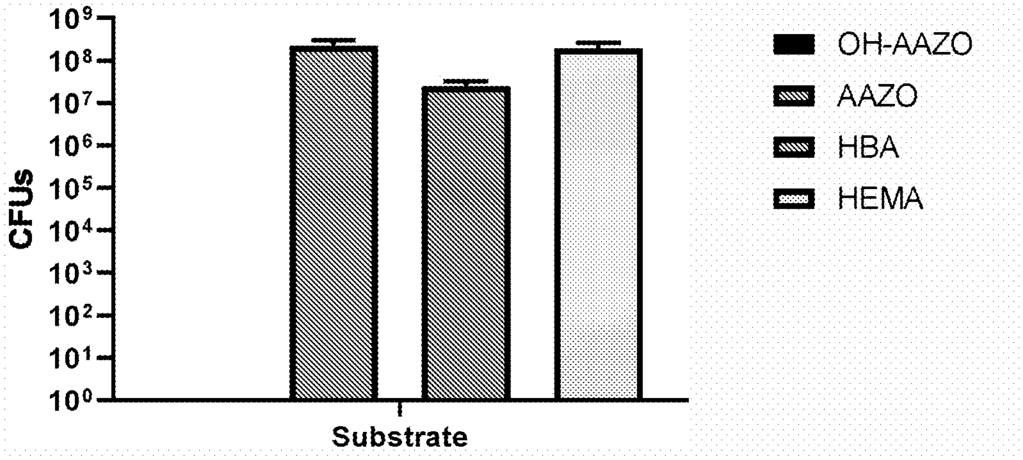
FIG. 14 is a graph of CFU values of biofilims growning on coatings generated from monomers with different functional groups to study the inhibitory effect. The biofilm growth was quantified at 24 h and shows that the antibacterial properties are specific to the OH-AAZO coatings.
Figure 15:
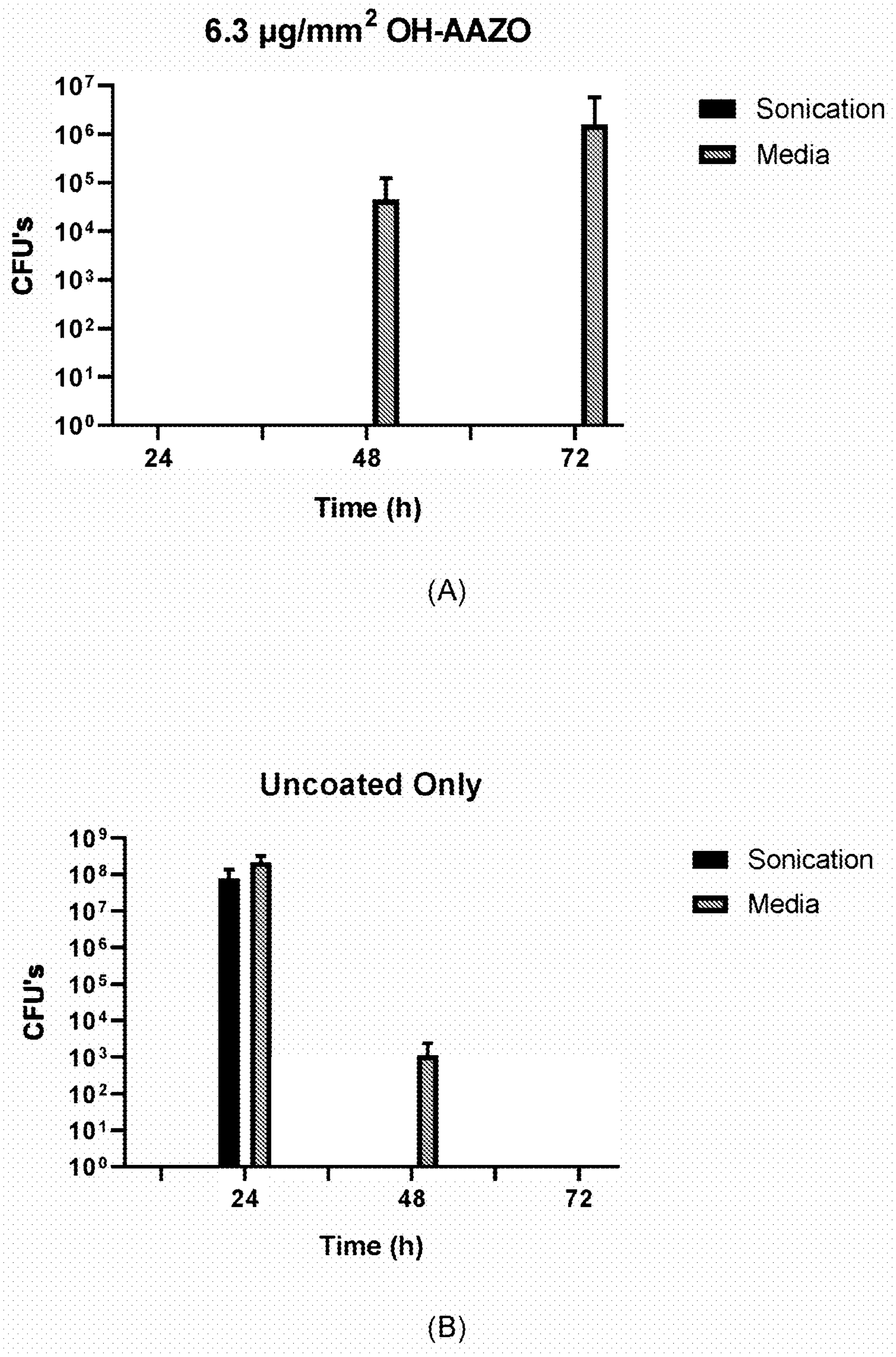
FIG. 15 are graphs of detachment study results over a 72 h timescale (all timepoints n≥3) for 50 mg/mL OH-AAZO coated substrates (FIG. 15 (A)) and the uncoated controls (FIG. 15 (B)), wherein "Media" corresponds to the amount of bacteria growing in the growth media surrounding the substrates at the indicated time and "Sonication" corresponds to the amount of bacterial removed from the substrates via sonication at the indicated time. Some media bacterial growth was observed at t=48 h and 72 h, likely due to variation in coating robustness. However, the substrates themselves maintained sterility over this 72 h timescale. The uncoated controls saw complete death on both the substrate and in the media, likely due to the depletion of media nutrients by the biofilm over time.

We prepared resin substrates coated with formulations of monomers AAZO (an acrylic azobenzene), HBA (an acrylic phenol), and HEMA (an aliphatic hydroxyl methacrylate) at concentrations of 50 mg/mL to observe *S. mutans* biofilm growth on their surfaces (all structures displayed in FIG. 14). Robust biofilms on the surface of AAZO, HBA, and HEMA-coated substrates were observed at 24 h ($10^7$-$10^8$ CFUs). Only the OH-AAZO coating achieved complete inhibition of *S. mutans* biofilm growth (0 CFUs, FIG. 14).

Membrane Potential Assay

Figure 19:
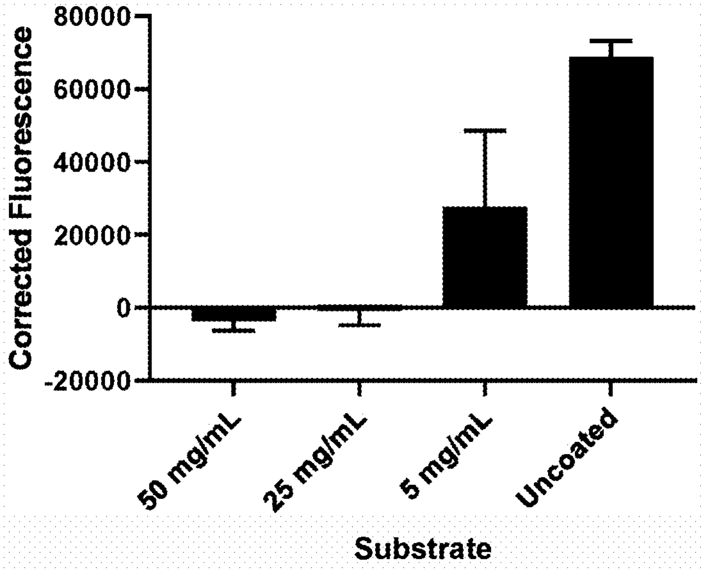
FIG. 19 is a graph shown the membrane potential assay results at different concentrations of coated OH-AAZO substrates. Raw data was corrected against the fluorescence values of the corresponding substrate (all raw values n=3).

A DIBAC4 (3) membrane potential assay was selected to quantify any decrease in metabolism in the biofilm cells. The DIBAC4 (3) assay results on *S. mutans* exposed to OH-AAZO showed a drop in fluorescence to zero at higher concentrations of OH-AAZO (50 mg/mL and 25 mg/mL), which is a sign of hyperpolarization of the membrane. There was a slight reduction in the 5 mg/mL OH-AAZO sample relative to an uncoated control (FIG. 19).

Monomer, Coating, and Substrate Formulations

Figure 8:
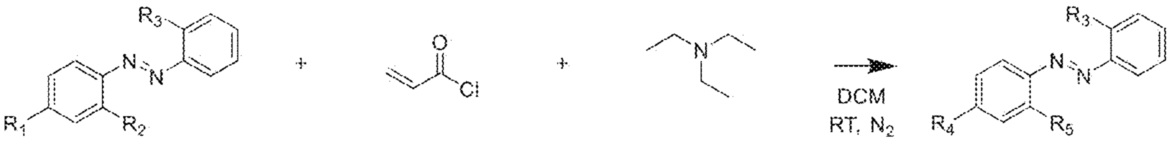
FIG. 8 is a synthetic schema of an acrylated azobenzene (AAZO, which is indentified as a) in FIG. 8), phenolic acrylated azobenzene (OH-AAZO, which is identified as b) in FIGS. 8), and 4-hydroxybenzyl acrylate (HBA) as a control monomer.
Figure 8:
Figure 8:
Figure 8:
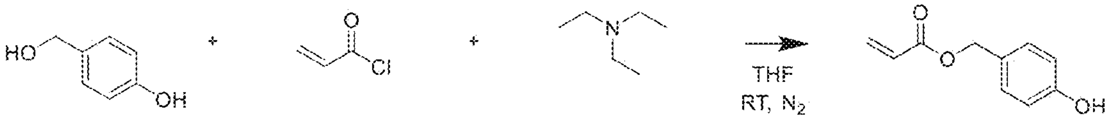

OH-AAZO was synthesized from a commercially available azobenzene using conventional acylation methods (FIG. 8). For the in vitro studies, methyl methacrylate, triethylene glycol dimethacrylate, and polymethyl methacrylate formulations (hereafter referred to as the substrate) were mixed in a ratio of 56:30:14 by weight and thermally cast in molds (80° C. for 1.5 h). The methacrylic C═C bond was monitored to ensure >95% double bond conversion via Fourier-Transformed Infrared spectroscopy.

The coating was prepared with a mixture of OH-AAZO in tetrahydrofuran (THF), azobisisobutyronitrile (AIBN, 2 wt. %, thermal initiator), and acrylated Rhodamine B (0.2 wt. % for imaging). THF was selected for more efficient packing and aggregation of the pendant azobenzene groups in the coating solution. Jeong et al., *High Energy Density in Azobenzene-based Materials for Photo-Thermal Batteries via Controlled Polymer Architecture and Polymer-Solvent Interactions*, Sci Rep. (2017), 7(1):1-12. The coating solutions were applied to the substrate via a spin-coating protocol and cured thermally at 100° C. The coated and uncoated substrates were subsequently extracted in MilliQ $H_2O$ and wet-autoclaved at 120° C. and 15 psi. The comprehensive extraction protocol of samples was implemented to ensure that there was complete absence of diffusible bactericidal materials from both the OH-AAZO coated and uncoated substrates. The coated and uncoated substrates were analyzed via UV-Vis to ensure the uniformity of the coating prior to use (FIG. 9).

Antibacterial Effect of OH-AAZO Against *S. mutans*

The antibacterial activity of OH-AAZO was observed to be concentration dependent. OH-AAZO coatings were prepared from coating solution concentrations of 100 mg/mL, 50 mg/mL, 25 mg/mL, and 5 mg/mL in THF, which correspond to OH-AAZO surface concentrations of 12.6 μg/$mm^2$, 6.3 μg/$mm^2$, 3.2 μg/$mm^2$, and 0.6 μg/$mm^2$, respectively, following application. Only at OH-AAZO concentrations of 50 mg/mL and above was the substrate and media able to achieve complete sterility (which we define here as 0 CFUs).

The selective elimination of cariogenic bacteria, such as *S. mutans*, without inducing microbial dysbiosis in the oral microbiota is critical to the success of the coating. Further biofilm quantification studies were performed with other oral bacterial strains *S. oralis* (Gram-positive, implicated in dental plaque formation and bacterial endocarditis) and *A. actinomycetemcomitans* (Gram-negative, periodontal disease-causing pathogen) to see if OH-AAZO would have an effect on their growth and proliferation as well. Do et al., *Population structure of Streptococcus oralis,* Microbiology (2009), 155(8):2593-2602. OH-AAZO coatings were also tested against biofilm-forming bacterial strains *S. aureus* and *E. coli* which are Gram-positive and Gram-negative, respectively. The antibacterial effect was only observed against the *S. oralis* biofilm, which suggested that the coating effect was specific to *Streptococci* species rather than Gram-positive or Gram-negative bacteria-specific effect (FIG. 17). It is believed that azobenzene molecules may be designed to specifically target pathogenic *Streptococci* while preserving beneficial and commensal species.

Towards developing a mechanistic understanding as to what specific functionality within the OH-AAZO molecule is responsible for the selective inhibition of *Streptococci*, we studied several other polymerized coatings containing similar structural moieties to OH-AAZO. In addition to OH-AAZO, the three monomers tested were AAZO (contains an azobenzene group but no hydroxyl group), HBA (contains a phenolic hydroxyl group but no azobenzene group), and HEMA (contains an aliphatic hydroxyl group but no azobenzene group). Only the OH-AAZO coating was successful in inhibiting *S. mutans* growth (FIG. 14). The structure-property implication of these results shows that the combination of azobenzenes and phenols give rise to the anti-*Streptococci* effect, which will be of great consideration for us as we design more molecules for antibacterial applications.

Figure 18:
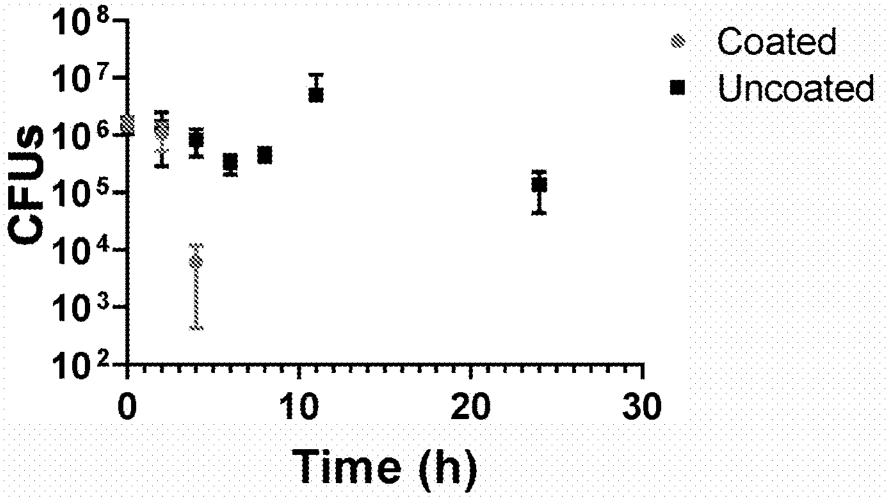
FIG. 18 is a graph showing the kill curve of *S. mutans* in media containing OH-AAZO coated substrates in comparison with an uncoated substrate over time. There is absence of *S. mutans* in the media surrounding the OH-AAZO substrate at t=6 h.

Interestingly, the presence of OH-AAZO at 50 mg/mL concentration prevented *S. mutans* biofilm formation not only on the substrate but also in the surrounding media, a phenomenon that was observed in all studies reported here. The substrates were aqueously extracted several times prior to use in order to avoid the unintentional release of solvents or small molecules that may kill the bacteria, which meant that only the tethered coating was responsible for the media bacteria death. Additional kinetic information was required to confirm the OH-AAZO coating's ability to induce cell death in the surrounding area as a function of time. Towards this end, we sampled media containing *S. mutans* with an OH-AAZO substrate to observe when the bacterial death occurs (FIG. 18). The results, which show complete *S. mutans* death by t=6 h following inoculation, confirm that the OH-AAZO substrate was successful in eliminating *S. mutans* not just from the surface of the OH-AAZO substrate but from the well as a whole in a relatively short amount of time following the initial exposure.

Currently ongoing studies in our lab are aimed at identifying the specific pathway by which the OH-AAZO coating is able to inhibit *Streptococci* biofilm growth and proliferation. For our preliminary studies on identifying the mechanism by which *Streptococci* biofilms are impacted by the coating, a DIBAC4(3) membrane potential assay was used. At 50 mg/mL OH-AAZO, the *S. mutans* fluorescence dropped to zero (FIG. 19), indicating disruption of ion homeostasis, which may ultimately be leading to cell death. Clearly, more detailed studies are required to establish the pathway via which the tethered OH-AAZO coatings are able to inhibit biofilm growth both on the substrate and in the surrounding media.

Our initial results indicate that the OH-AAZO has the potential to form a *Streptococci*-selective antibacterial coating. Establishing biochemical pathways that are affected by the selective inhibition observed here will be utilized to design more potent, cytocompatible antibacterial coatings that can selectively inhibit multiple species and provide a toolkit to tailor and edit microbiomes.

General Terminology and Interpretative Conventions

Any methods described in the claims or specification should not be interpreted to require the steps to be performed in a specific order unless expressly stated otherwise. Also, the methods should be interpreted to provide support to perform the recited steps in any order unless expressly stated otherwise.

Certain features described in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Articles such as "the," "a," and "an" can connote the singular or plural. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y).

The term "and/or" shall also be interpreted to be inclusive (e.g., "x and/or y" means one or both x or y). In situations where "and/or" or "or" are used as a conjunction for a group of three or more items, the group should be interpreted to include one item alone, all the items together, or any combination or number of the items.

The terms have, having, include, and including should be interpreted to be synonymous with the terms comprise and comprising. The use of these terms should also be understood as disclosing and providing support for narrower alternative implementations where these terms are replaced by "consisting" or "consisting essentially of."

Unless otherwise indicated, all numbers or expressions, such as those expressing dimensions, physical characteristics, and the like, used in the specification (other than the claims) are understood to be modified in all instances by the term "approximately." At the very least, and not as an attempt to limit the application of the doctrine of equivalents to the claims, each numerical parameter recited in the specification or claims which is modified by the term "approximately" should be construed in light of the number of recited significant digits and by applying ordinary rounding techniques.

All disclosed ranges are to be understood to encompass and provide support for claims that recite any subranges or any and all individual values subsumed by each range. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth), which values can be expressed alone or as a minimum value (e.g., at least 5.8) or a maximum value (e.g., no more than 9.9994).

All disclosed numerical values are to be understood as being variable from 0-100% in either direction and thus provide support for claims that recite such values (either alone or as a minimum or a maximum—e.g., at least <value> or no more than <value>) or any ranges or subranges that can be formed by such values. For example, a stated numerical value of 8 should be understood to vary from 0 to 16 (100% in either direction) and provide support for claims that recite the range itself (e.g., 0 to 16), any subrange within the range (e.g., 2 to 12.5) or any individual value within that range expressed individually (e.g., 15.2), as a minimum value (e.g., at least 4.3), or as a maximum value (e.g., no more than 12.4).

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used in this document shall mean" or similar language (e.g., "this term means," "this term is defined as," "for the purposes of this disclosure this term shall mean," etc.). References to specific examples, use of "i.e.," use of the word "invention," etc., are not meant to invoke exception (b) or otherwise restrict the scope of the recited claim terms.

Other than situations where exception (b) applies, nothing contained in this document should be considered a disclaimer or disavowal of claim scope.

The subject matter recited in the claims is not coextensive with and should not be interpreted to be coextensive with any implementation, feature, or combination of features described or illustrated in this document. This is true even if only a single implementation of the feature or combination of features is illustrated and described.

Chemistry

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A polymeric composition comprising:

a polymer chain in a dental resin-based composite; and an azobenzene pendant group attached to the polymer chain, wherein the azobenzene pendant group includes a N═N double bond group and a phenyl ring having a hydroxyl substituent group, and wherein the azobenzene pendent group is attached via a linking group to the polymer chain at a ring carbon atom ortho to the N═N double bond group.

2. The polymeric composition of claim 1, wherein the azobenzene pendant group has the following structure:

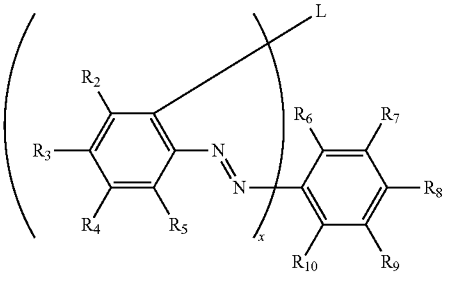

wherein:

x is an integer from 1 to 10;

L is a linking group that links the structure to the polymer chain in a dental resin-based composite; and R2, R3, R4, R5, R6, R7, R8, R9, and R10 are independently selected from H, methyl, and hydroxyl, and wherein at least one of R2, R3, R4, R5, R6, R7, R8, R9, or R10 is hydroxyl.

3. The polymeric composition of claim 2, wherein L is a (meth)acrylate linking group.

4. The polymeric composition of claim 2, wherein x is 1.

5. The polymeric composition of claim 2, wherein at least one of R7, R8, or R9 is hydroxyl.

6. The polymeric composition of claim 2, wherein x is 1; L is a (meth)acrylate linking group; and at least one of R7, R8, or R9 is hydroxyl.

7. The polymeric composition of claim 2, wherein x is 1; L is a (meth)acrylate linking group; and at least one of R6 is hydroxyl.

8. The polymeric composition of claim 1, wherein the azobenzene pendant group has the following structure:

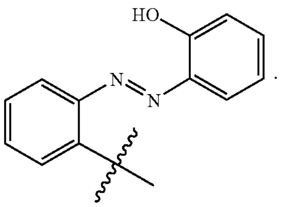 [SMILES: *c1ccccc1/N=N/c1ccccc1O]

9. A method of making the polymeric composition of claim 1, comprising reacting an azobenzene monomer with the polymer chain in the dental resin-based composite to form the polymeric composition comprising the azobenzene pendant group attached to the polymer chain, wherein the azobenzene monomer includes a N═N double bond group and a phenyl ring having a hydroxyl substituent group.

10. The method of claim 9, wherein the azobenzene pendant group has the following structure:

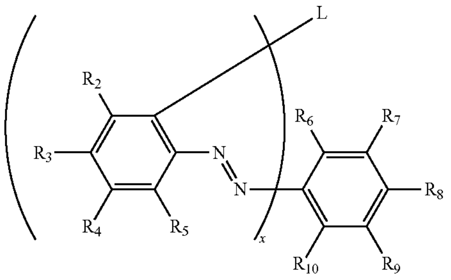

wherein:

x is an integer from 1 to 10;

L is a linking group that links the structure to the polymer chain in a dental resin-based composite; and R2, R3, R4, R5, R6, R7, R8, R9, and R10 are independently selected from H, methyl, and hydroxyl, and wherein at least one of R2, R3, R4, R5, R6, R7, R8, R9, or R10 is hydroxyl.

11. The method of claim 10, wherein L is a (meth)acrylate linking group.

12. The method of claim 10, wherein x is 1.

13. The method of claim 10, wherein at least one of R7, R8, or R9 is hydroxyl.
14. The method of claim 10, wherein x is 1, L is a (meth)acrylate linking group, and at least one of R7, R8, or R9 is hydroxyl.
15. The method of claim 10, wherein x is 1, L is a (meth)acrylate linking group; and at least R6 is hydroxyl.
16. The method of claim 9, wherein the azobenzene pendant group has the following structure:
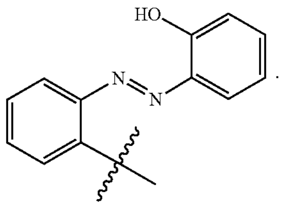 [SMILES: *c1ccccc1/N=N/c1ccccc1O]
* * * * *